US008088759B2

(12) United States Patent
Glick

(10) Patent No.: US 8,088,759 B2
(45) Date of Patent: Jan. 3, 2012

(54) 1,4-BENZODIAZEPINE-2,5-DIONES WITH THERAPEUTIC PROPERTIES

(75) Inventor: Gary D. Glick, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 1020 days.

(21) Appl. No.: 11/591,324

(22) Filed: Nov. 1, 2006

(65) Prior Publication Data

US 2007/0111994 A1 May 17, 2007

Related U.S. Application Data

(60) Provisional application No. 60/732,045, filed on Nov. 1, 2005.

(51) Int. Cl.
*A01N 43/00* (2006.01)
*A61K 31/33* (2006.01)
*C07D 487/00* (2006.01)
*C07D 243/12* (2006.01)
*C07D 221/00* (2006.01)
*C07D 223/04* (2006.01)
*C07J 71/00* (2006.01)

(52) U.S. Cl. .......... 514/183; 540/498; 540/504; 540/54; 540/204; 540/610

(58) Field of Classification Search .......... None
See application file for complete search history.

(56) References Cited

U.S. PATENT DOCUMENTS

| 3,261,828 A | 7/1966 | Uskokovic |
| 3,374,264 A | 3/1968 | Uskokovic |
| 3,384,635 A | 5/1968 | Calabateas |
| 3,415,814 A | 12/1968 | Calabeteas |
| 3,847,905 A | 11/1974 | Bub |
| 4,076,823 A | 2/1978 | Wade |
| 4,088,756 A | 5/1978 | Voorhees |
| 4,108,852 A | 8/1978 | Bub |
| 4,110,337 A | 8/1978 | Szarvasi |
| RE30,293 E | 6/1980 | Bub |
| 4,495,101 A | 1/1985 | Klaubert |
| 4,551,480 A | 11/1985 | Stiefel |
| 4,560,684 A | 12/1985 | Sugasawa |
| 4,623,646 A | 11/1986 | Casals-Stenzel |
| 4,751,223 A | 6/1988 | Glamkowski |
| 4,820,834 A | 4/1989 | Evans |
| 4,894,366 A | 1/1990 | Okuhara |
| 4,898,861 A | 2/1990 | Morgan |
| 4,916,138 A | 4/1990 | Ueda |
| 4,929,611 A | 5/1990 | Okuhara |
| 4,946,778 A | 8/1990 | Ladner |
| 5,004,741 A | 4/1991 | Evans |
| 5,041,438 A | 8/1991 | Hsu |
| 5,141,930 A | 8/1992 | Nakao |
| 5,147,872 A | 9/1992 | Golwyn |
| 5,216,148 A | 6/1993 | Klaus |
| 5,288,514 A | 2/1994 | Ellman |
| 5,324,726 A | 6/1994 | Bock |
| 5,391,566 A | 2/1995 | Chakravarty |
| 5,444,092 A | 8/1995 | Collins |
| 5,521,170 A | 5/1996 | Setoi |
| 5,545,568 A | 8/1996 | Ellman |
| 5,559,230 A | 9/1996 | Ogawa |
| 5,591,227 A | 1/1997 | Dinh |
| 5,597,915 A | 1/1997 | Chambers |
| 5,599,352 A | 2/1997 | Dinh |
| 5,633,251 A | 5/1997 | Claremon |
| 5,677,282 A | 10/1997 | Oleksyszyn |
| 5,697,967 A | 12/1997 | Dinh et al. |
| 5,763,437 A | 6/1998 | Sato |
| 5,776,946 A | 7/1998 | McGeer |
| 5,861,380 A | 1/1999 | Gyorkos |
| 5,962,337 A | 10/1999 | Ohlmeyer |
| 6,004,942 A | 12/1999 | Firestein |
| 6,074,859 A | 6/2000 | Hirokawa |
| 6,080,568 A | 6/2000 | Day |
| 6,100,254 A | 8/2000 | Budde |
| 6,239,131 B1 | 5/2001 | Shinozaki |
| 6,277,844 B1 | 8/2001 | Spector |
| 6,319,931 B1 | 11/2001 | Kroemer |
| 6,506,744 B1 | 1/2003 | Alig |
| 6,524,623 B1 | 2/2003 | Hodosh |
| 6,524,832 B1 | 2/2003 | Kufe |
| 2,457,405 A1 | 3/2003 | Glick |

(Continued)

FOREIGN PATENT DOCUMENTS

CA 2372150 11/2000

(Continued)

OTHER PUBLICATIONS

Patani, George, et al , "Bioterrorism: A Rational Approach to Drug Design," Chem. Rev., vol. 96, pp. 3147-3176 (1996).* International Search Report, International Patent Application No. PCT/US04/013455 dated Jan. 6, 2006.
European Search Report, EP Patent Application No. 03 027 484.9-2117 dated May 3, 2004.
European Search Report, EP Patent Application No. 04 775 923.8-2123 dated Nov. 9, 2007.
European Search Report, EP Patent Application No. 00 928 586.7-2117 dated Apr. 23, 2002.
European Search Report, EP Patent Application No. 05 769 345.9 dated Oct. 22, 2007.
International Search Report, PCT/US2006/042753, dated May 6, 2008.
Written Opinion of the International Searching Authority, PCT/US06/21561, dated Aug. 17, 2007.
International Preliminary Report on Patentability, PCT/US2006/041446, mailed May 8, 2008.
International Search Report and Written Opinion, PCT/US2006/00442, mailed May 12, 2006.

(Continued)

*Primary Examiner* — Jeffrey S. Lundgren
*Assistant Examiner* — William Lee
(74) *Attorney, Agent, or Firm* — Casimir Jones SC

(57) ABSTRACT

The present invention relates to novel chemical compounds, methods for their discovery, and their therapeutic use. In particular, the present invention provides novel 1,4-benzodiazepine-2,5-dione compounds, and methods of using novel 1,4-benzodiazepine-2,5-dione compounds as therapeutic agents to treat a number of conditions associated with the faulty regulation of the processes of programmed cell death, autoimmunity, inflammation, hyperproliferation, and the like.

14 Claims, 15 Drawing Sheets

U.S. PATENT DOCUMENTS

| | | |
|---|---|---|
| 6,579,854 B1 | 6/2003 | Mitchell |
| 6,605,593 B1 | 8/2003 | Naicker |
| 6,613,739 B1 | 9/2003 | Naicker |
| 6,767,533 B1 | 7/2004 | Casellas |
| 6,824,561 B2 | 11/2004 | Soykan |
| 6,916,813 B2 | 7/2005 | Atwal |
| 7,125,866 B1 | 10/2006 | Glick |
| 7,144,880 B2 | 12/2006 | Glick |
| 7,150,433 B2 | 12/2006 | Healy |
| 7,175,953 B2 | 2/2007 | Licha |
| 7,220,739 B2 | 5/2007 | Glick |
| 7,250,410 B2 | 7/2007 | Bourguignon |
| 7,276,348 B2 | 10/2007 | Glick |
| 7,351,241 B2 | 4/2008 | Bendett |
| 7,572,788 B2 | 8/2009 | Glick |
| 7,638,624 B2 | 12/2009 | Glick |
| 7,683,046 B2 | 3/2010 | Glick |
| 7,851,465 B2 | 12/2010 | Glick |
| 2002/0025946 A1 | 2/2002 | Buchanan |
| 2002/0048566 A1 | 4/2002 | El-Deiry |
| 2002/0128208 A1 | 9/2002 | Snyder |
| 2003/0044776 A1 | 3/2003 | Dykens |
| 2003/0119029 A1 | 6/2003 | Glick |
| 2004/0009972 A1 | 1/2004 | Ding |
| 2004/0087489 A1 | 5/2004 | Ruiz |
| 2004/0157833 A1 | 8/2004 | Harris |
| 2004/0176358 A1 | 9/2004 | Glick |
| 2005/0113460 A1 | 5/2005 | Glick |
| 2005/0261176 A1 | 11/2005 | Glick |
| 2005/0272723 A1 | 12/2005 | Glick |
| 2006/0025388 A1 | 2/2006 | Glick |
| 2006/0052369 A1 | 3/2006 | Glick |
| 2006/0166975 A1 | 7/2006 | Glick |
| 2007/0036854 A1 | 2/2007 | Glick |
| 2007/0043033 A1 | 2/2007 | Glick |
| 2007/0105844 A1 | 5/2007 | Glick |
| 2007/0111994 A1 | 5/2007 | Glick |
| 2007/0135418 A1 | 6/2007 | Glick |
| 2007/0299059 A1 | 12/2007 | Glick |
| 2008/0064686 A1 | 3/2008 | Durrani |

FOREIGN PATENT DOCUMENTS

| | | |
|---|---|---|
| CA | 2457405 | 2/2003 |
| CA | 2372150 | 11/2007 |
| DE | 1810423 | 10/1969 |
| EP | 0 349 949 | 1/1990 |
| EP | 0227539 | 5/1990 |
| EP | 0 906 907 | 7/1999 |
| EP | 1143946 | 10/2001 |
| EP | 1423122 | 2/2003 |
| EP | 1398033 | 3/2004 |
| EP | 1622684 | 2/2006 |
| EP | 1742460 | 7/2006 |
| EP | 1778204 | 5/2007 |
| EP | 1786429 | 5/2007 |
| EP | 1845996 | 10/2007 |
| GB | 1363735 | 8/1974 |
| RU | 2096044 | 11/1997 |
| WO | 90/05305 | 5/1990 |
| WO | 90/13332 | 11/1990 |
| WO | 91/12779 | 9/1991 |
| WO | 92/01683 | 2/1992 |
| WO | 94/08234 | 4/1994 |
| WO | 97/01560 | 1/1997 |
| WO | 97/30992 | 8/1997 |
| WO | 98/14192 | 4/1998 |
| WO | 98/57161 | 12/1998 |
| WO | 99/19306 | 4/1999 |
| WO | 99/29347 | 6/1999 |
| WO | 99/58117 | 11/1999 |
| WO | 99/66958 | 12/1999 |
| WO | 99/67220 | 12/1999 |
| WO | 00/19200 | 6/2000 |
| WO | 00/66106 | 11/2000 |
| WO | WO 00/66106 | * 11/2000 |
| WO | 01/51922 | 7/2001 |
| WO | 02/067988 | 9/2002 |
| WO | 02/098865 | 12/2002 |
| WO | 03/015703 | 2/2003 |
| WO | 03/014658 | 5/2003 |
| WO | 03/045901 | 6/2003 |
| WO | 03/050261 | 6/2003 |
| WO | 03/106628 | 12/2003 |
| WO | 2005/004988 | 1/2005 |
| WO | 2006/014526 | 2/2006 |
| WO | 2006/029245 | 3/2006 |
| WO | 2006/073448 | 7/2006 |
| WO | 2006/074358 | 7/2006 |
| WO | 2006/053193 | 5/2007 |
| WO | 2007/050587 | 5/2007 |
| WO | 2007/053725 | 5/2007 |
| WO | 2007/146167 | 12/2007 |
| WO | 2008/012553 | 9/2008 |
| WO | 2008/116156 | 9/2008 |
| WO | 2008/133635 | 11/2008 |
| WO | 2009/061916 | 5/2009 |

OTHER PUBLICATIONS

International Report on Patentability, PCT/US2006/000442 mailed Jul. 12, 2007.
Puodziunaite, B., et al., "Bromination of Aromatic Ring of Tetrahydro-1,5-Benzodiazepin-2-Ones", Chemistry of Heterocyclic Compounds, vol. 36, No. 6, 2000.
AU Examiners Report, AU Patent App. No. 2005323519 dated Nov. 27, 2007.
EP Search, EP Patent App. No. 03 027 484.9-2117, dated Jan. 31, 2005.
Canadian Patent Search, CA Patent Application No. 2,457,405, dated Feb. 6, 2007.
Wolvetang, et al., FEBS Letters (1994), 339, 40-44.
Nawrocka, et al., Arch. Pharm. (Weinheim) Jan. 2001, 334(1), 3-10.
International Search Report and Written Opinion, PCT/US08/56231, mailed Jun. 24, 2008.
International Search Report and Written Opinion, PCT/US05/14463, mailed Dec. 4, 2006.
International Search Report and Written Opinion, PCT/US07/11422, mailed Nov. 15, 2007.
International Search Report and Written Opinion, PCT/US07/13576, mailed Nov. 23, 2007.
International Search Report, PCT/US06/042753, mailed Apr. 19, 2007.
Desjardins, P and Stephanie Ledoux, "The Role of Apoptosis in Neurodegenerative Disease," Metabolic Brian Disease, vol. 13, No. 2, pp. 79-96 (1998).
International Search Report, PCT/US06/41446, mailed Aug. 1, 2007.
GODIC, "New approaches to psoriasis treatment. A review." 2004. Acta Dermatoven APA, vol. 13, No. 2, pp. 50-57.
Bisaha, S.N., et al., A switch in enantiomer preference between mitochondrial F1F0-ATPase chemotypes, Bioorganic & Medicinal Chemistry Letters, 2005 15(11), pp. 2749-2751.
International Search Report and Written Opinion dated Mar. 27, 2009, PCT/US2008/076021.
Thompson, C.B., "Apoptosis in the Pathogenesis and Treatment of Disease," Science 267:1456-1462 (1995).
Ursini et al., "Synthesis and SAR of New 5-Phenyl-3-ureido-1,5-benzodiazepines as cholecystokinin-B receptor antagonists", J. Med. Chem. 43 (2000) 3596-3613.
Walser, et al., "Quinazolines and 1,4-benzodiazepines. LILX. Preparation of Pyrrolo[2,1-c]-1,4-benzodiazepin-2-ones", J. Org. Chem. 38:3502-3507 (1973).
Watanabe-Fukunaga, R., et al., "Lymphoproliferation Disorder in Mice Explained by Defects in Fas Antigen that Mediates Apoptosia,"Nature 356:314-317 (1992).
White, E., "Life, Death, and the Pursuit of Apoptosis," Genes & Development 10:1-15 (1996).
Williams, D. et al, "Identification of compounds the bind mitochondrial F1F0 ATPase by screening a triazine library . . . " Chemistry & Biol. 11:1251-1259, 9(2004).
Wu, G.Y., et al., "Receptor-Mediated in Vitro Gene Transformation by a Soluble DNA Carrier System," The Journal of Biological Chemistry 262(10):4429-4432 (1987).

Wyllie, A.H., "The Genetic Regulation of Apoptosis," Current Opinion in Genetics & Development 5:97-104 (1995).

Zamzami, N., et al., "Mitochondrial Control of Nuclear Apoptosis," J. Exp. Med. 183:1533-1544 1996.

Zoratti, M., et al., "The Mitochondrial Permeability Transition," Biochimica et Biophysica Acta 1241:139-176 (1995).

International Search Report, International Patent Application No. PCT/US05/24060, dated Dec. 13, 2006.

International Search Report, International Patent Application No. PCT/US02/26171 dated Aug. 8, 2003.

International Search Report, International Patent Application No. PCT/US01/11599 dated Mar. 6, 2001.

International Search Report, International Patent Application No. PCT/US005/031942 dated Sep. 21, 2006.

Gupta et al., "Psychitripic drugs in dermatology . . . " Database:EMbase (AN:86111413), Journal of the American Academy of Dermatology, 1986, vol. 14, No. 4, pp. 633-645.

Lowe, "Systemic treatment of severe psoriasis," The New England Journal of Medicine, 324 (5), Feb. 7, 1991, pp. 333-334.

Laupacis, et al., "Cyclosporin A: a powerful immunosuppressant", CMA Journal, May 1, 1982, vol. 126, pp. 1041-1046.

Otto, M.W., et al. (2005) J. Clin. Psychiatry 66 Suppl. 2:34-38.

Yoshi, M., et al., (2005) Nippon Yakurigaku Zasshi 125(1):33-36.

Yasuda, K., (2004) Nippon Rinsho. 62 Suppl. 12:360-363.

Dacaudin, D. (2004) 15(8):737-745.

Bonnot, O., et al., (2003) Encephale. 29(6):553-559.

International Search Report and Written Opinion, PCT/US2008/082629, mailed Jun. 1, 2009.

Lacapere, J.J., et al. (2003) Steroids 68(7-8):569-585.

Galiegue, S., et al. (2003) Curr. Med. Chem (10(16):1563-1572.

Papadopoulo, V. (2003) Ann. Pharm. Fr. 61(1):30-50.

Goethals, I., et al. (2003) Eur. J. Nucl. Med. Mol. Imaging 30(2):325-328.

Casedo, M., et al. (2002) J. Exp. Med. 196(9):1121-1125.

Buffett-Jerrott S.E. et al. (2002) Curr. Pharm. Des. 8(1):45-58.

Smyth, W.F., et al. (1998) Electrophoresis 19(16-17):2870-2882.

Yoshii, M., et al. (1998) Nihon Shinkeo Seishin Yakurigaku Zasshi, 18(2):49-54.

Varani, J., et al., "A Novel Benzodiazepine Selectively Inhibits Keratinocyte Proliferation . . . ", The Journal of Pharmacology and Experimental Therapeutics, 2005, vol. 313, No. 1, pp. 56-63.

Varani, J., et al. (2001), J. Invest. Dermatol., 117:1335-1341.

Varani, et al., (1994), J. Clin. Invest., 94:1747-1753.

Griffith, C.E., Br. J. Dermatol., Apr. 2001; 144(4):679-81.

Stern, R.S. (1995), dERMATOL. cLIN. 13:717-722.

Fry, L (1988), Brit. J. Dermatol., 119:445-461.

Krueger GC, et al., (1984), J. Am. Acad. Dermatol., 11:937-947.

EP Supplementary Search Report, EP Application No. 02794914.8 dated Nov. 6, 2008.

Lee, et al., J. Org. Chem. 1999, 64, 3060-3065.

Solomko, et al., Chemistry of Heterocyclic Compounds, vol. 11, No. 11, Nov. 1975, pp. 1231-1248.

EP Patent Application No. 05 80 4417 Supplementary European Search Report dated Mar. 26, 2009.

Algarra, et al., "Application of the Photo-Fries Rearrangement of Aryl N-Chloroacetylanthranylates as Key Step in the . . . ", Heterocycles, vol. 36 1993, pp. 2335-2344.

EP Patent Application No. 06 717616 Supplementary Search Report dated Mar. 26, 2009.

Levitzki, Alexander, "Protein Tyrosine Kinase Inhibitors as Novel Therapeutic Agents," Pharmacol. Ther. vol. 82, Nos. 2-3, pp. 231-239 (1999).

Sanchez, et al., "Tumorigenic activity of the BCR-ABL oncogenes is mediated by BCL2" Proc Natl Acad Sci U S A (Jun. 6, 1995) 92(12) 5287-5291.

Ji Yang, et al., "Prevention of Apoptosis by BCL-2; Release of Cytochrome c from Mitochondria Blocked" Science vol. 275, No. 5303, pp. 1129-113221 (1997).

Prindull, "Apoptosis in the embryo and tumorigenesis" European Journal of Cancer, vol. 31, Issue 1 (1995) pp. 116-123.

Kerver et al, "In situ detection of spontaneous superoxide anion and singlet oxygen production by mitochondria in . . . ", Histochem. J., 29:229-237 [1997] (Abstract only).

Kim et al., "Synthesis of 3-substituted 1,4-benzodiazepin-2-ones," J. Braz. Chem. Soc. 9:375-379 (1998).

Kohler and Milstein, "Continuous cultures of fused cells . . . ", Nature, 256:495-497 [1975].

Koopman, W.J., et al., "The MRL-lpr/lpr Mouse. A Model for the Study of Rheumatoid Arthritis," Scan& J. Rheumatolo Suppl 75:284-o289 (1988).

Korsmeyer, S.J., "Bcl-2 Initiates a New Category of Oncogenes: Regulators of Cell Death," Blood 80(4):879-886 1992.

Kozbor, et al. •"The production of monoclonal antibodies from human lymphocytes", Immunol. Today, 4:72 [1983].

Lee, Sunwoo, et al., "Improved Catalysts for the Palladium-Catalyzed Synthesis of Oxindoles by . . . ", J. Org. Chem. 2001, 66, pp. 3402-3415.

Lewis et al., "Editors' view: Cancer pharmacotherapy: 21st century 'magic bullets' and changing paradigms", British Journal of Clinical Pharmacology, 2006, 62:1,pp. 1-4.

Liu, J.R., et al., "Bclox•. is Expressed in Ovarian Carcinoma and Modulates Chemotherapy-induced Apoptosis," Gynecologic Oncology 70:398-403 (1998).

Los, M., et al., The Role of Caspases in Development, Immunity, and Apoptotic Signal Transduction: Immunity-10:629-639 (1999).

Lowman, et al., "Mutational analysis and protein engineering of receptor-binding determinants in human placental lactogen", J. Biol. Chem. 266:10982 [1991].

Luria,et al., "Tumor Viruses", General Viology 3rd edition,. 436-446 (1978)—Eds. John Wile & Sons, New York.

Malgrange, B., et al., "I-Carbolines Induce Apoptotic Death of Cerebellar Granule Neurones in Cultures," NeuroReport 7(18):3041-3045 (1996).

Marino, M., et al., "Prevention of Systemic Lupus Erythematosus in MRL/Ipr Mice by Administration of an Immunoglobulin . . . , " Nature Biotechnology -18:735-739 (2000).

McDonnell—349:254-256T J et al., Progression from Lymphoid Hyperplasia to High-Grade . . . Nature—349:254-256 (1991).

Miccoli, et al., "Potentiation of Lonidamine and Diazepam . . . ", Journal of the National Cancer Institute, vol. 90, No. 18, pp. 1400-1406, Sep. 1998.

Miernik et al., "The antimitotic activities of some benzodiazepines", Experientia, 1986, 42, pp. 956-958.

Miller, K.A., et al., "Benzodiazepines Prevent Neuronal Death by Apoptosis & Necrosis . . . , " Society for Neuroscience Abstracts—24(1-2):929 (1998).

Monks, A., et., Feasibility of High-Flux Anticancer Drug Screen Using a Diverse Panel of Cultured Human Tumor Cell Lines, Journal of the National Cancer Institute, 83:757-766 (1991).

Nagata, S., "Human Autoimmune Lymphoproliferative Syndrome, a Defect in the Apoptosis-Inducing Fas Receptor: A 55 Lesson from the Mouse Model," J. Hum. Genet 43:2-8 (1998).

Okuyama, H., et al., "Analysis of Defective Delayed-Type Hypersensitivity in Autoimmune Mice Bearing Ipr Gene," Clln. Ex p. ImmunoL 63:87-94 1986.

Okuyama, H., et al., "Effect of Cyclophosphamide Pretreatment on Defective Delayed-Type Hypersensitivity . . . , " Int Arch. Allergy Appl. Immunol. 88:394-40 (1989).

Ozols, R.F., "Paclitaxel Plus Carboplatin in the Treatment of Ovarian Cancer," Seminars in Oncology 26(1) (Supp.2:84-89 (1999).

Paola Costantini et al., "Mitochondrion as Novel Target of Anticancer Chemotherapy", JNCI Journal of the National Cancer Institute 2000 92(13): 1042-1053; doi:10. 1093/jnci/92. 13. 1042. (2000).

Parks, Daniel J. "1,4-benzodiazepine-2,5-diones as small molecule antagonists of the HDM2-p53 interaction . . . " Bioorg Med Chem. Ltrs,. 15,(2005), 765-770.

Paull, K.D., et al., "Display and analysis of patterns of differential activity of drugs against human tumor . . . ", J. Natl. Cancer Inst., 81:1088-1092 [1989] (Abstract only).

Pestell, K.E., et al., "Charactehsation of the P53 Status, BCL-2 Expression and Radiation and Platinum Drug Sensitivity of . . . , " Int J. Cancer—77:913-918 (1998).

Raboisson, P. "Structure-based design, synthesis and biological evaluative of novel 1,4-diazepines as HDM2 antagonists," Bioorg Med Chem. Ltrs., 15,(2005), 1857-1861.

Ramdas et al., "Benzodiazepine compounds as inhibitors of the Src protein tyrosine kinase . . ." Archives of Biochemistry and Biophysics 368 (1999) 394-400.

Raynaud, F.I., et al., "Intracellular Metabolism of the Orally Active Platinum Drug JM216: Influence of Glutathione Levels," Br. J. Cancer 74(3) :380-?386 (1996).

Russell, J.H., et al., "Mature T Cells of Autoimmune lpr/lpr Mice have a Defect in Antigen-Stimulated Suicide,"Proc. Nat. Acad. Sci. USA 90:4409-4413 (1993).

Sakata, K., et al., "Role of Fas/FasL Interaction in Physiology and Pathology: The Good and the Bad," Clinical Immunology and Immunopathology 87(1):1-7 (1998).

Sandstrom, P.A., et al., Autocrine Production of Extracellular Catalase Prevents Apoptosis.. Proc. Natl. Acad. Sci. USA-90:4708-4712 (1993).

Schlumpf, M., et al., "Delayed Developmental Immunotoxicity of Prenatal Benzodiazepines,"Toxic. In Vitro—8 (5):1061-1065(1994).

Schoemaker, H., et al., "Specific High-Affinity Binding Sites for [3H]Ro5—4864 in Rat Brain and Kidney," The J. of Pharm and Experimental Therapeutics—225(1)61-69 (1983).

Schwab, M., et al., "Amplified DNA with Limited Homology to myc Cellular Oncogene is Shared by Human Neuroblastoma Cell Lines and . . . ," Nature-305:245-248 (1983).

Scott, C.F., et al., "Comparison of Antigen-Specific T Cell Responses in Autoimmune MRL/mp-Ipr/lpr and MRUMp-++ Mice," The Journal of Immunology—1322:633-639 (1994_.

Sentman, C.L., et al., "bcl-2 Inhibits Multiple Forms of Apoptosis but not Negative Selection in Thymocytes," Cell 67:879-886 (1991).

Shaughnessy, Kevin, H., et al., "Palladium-Catalyzed Inter- and Intramolecular . . . " J. Org. Chem. 1998, 63, pp. 6546-6553.

Sheppard, R.C., et al., "Acid-Labile Resin Linkage Agents for Use in Solid Phase Peptide Synthesis;" Int J. Peptide Protein Res. 20:451-454 (1982).

Snyder, Jane R., et al, "Dissection of melanogenesis with small molecules identifies prohibition as a regulator", Chemistry & Biol. 12:477-484, 4(2005).

Stevens, S.Y., et al., "Non Nucleic Acid Inhibitors of Protein-DNA Interactions Identified Through Combinatorial Chemistry," J. Am. Chem.Soc.—118:10650-10651 (1996).

Sugimoto, T., et al., Determination of Cell Surface Membrane Antigens . . . JNCI-73: (1):51-57 (1984).

Swanson et al, "Ligand recognition by anti-DNA Autoantibodies," Biochemistry, 35:1624-1633 [1996] (Abstract only).

Swanson, P.C., et al., "Ligand Recognition by Murine Anti-DNA Autoantibodies," J. Clin. Invest 97(7):1748-1760 (1996).

Swanson, P.C.,et al., "High Resolution Ephope Mapping of an Anti-DNA Autoantibody Using Model DNA Ligands," J. Immunology 71 152(5):2601-2612 (1994).

Takahashi, T., et al., "Generalized Lymphoproliferative Disease in Mice, Caused by a Point Mutation in the Fas Ligand;" Cell 76:969-976 (1994).

Tanimoto, Y., et al., Benzodiazepine Receptor Agonists Modulate Thymocyte Apoptosis Through Reduction of the Mitochondrial . . . Jpn. J. Pharmacol. 79:177-183 (1999).

Taupin, V., et al., Endogenous Anxiogenic peptide, ODN-Diazepam-Binding Inhibitor, and Benzodiazepines.. Lymphokine and Cytokine Research 10(1):7-13 (1991).

Theoffopoulous, AN, et al., "Murine Models of Systemic Lupus Erythematosus," Advances in Immunology 37:269-390 (1985).

AU Patent Application No. 2006203946 Examiner's Report dated Sep. 10, 2008.

EP Search, EP Patent Application No. 05856659, mailed Dec. 9, 2008.

Iiangumaran, et al., "CD44 Selectively Associates with Active Src Family Protein Tyrosine Kinases Lck and Lyn in Glycosphingolipid-Rich . . . ", Blood, vol. 91, No. 10 (May 15, 1998), pp. 3901-3908.

Sato, et al., "CD22 negatively and positively regulates signal transduction through the B lymphocyte antigen receptor," seminars in Immunology, vol. 10, 1998, pp. 287-297.

Joshi, et al., "Oligomycin Sensitivey-conferring Protein (OSCP) of Mitochodrial ATP Synthase," The Journal of Biological Chemistry, Vol. 267, No. 18,m Issue of Jun. 25, pp. 12860-12867, 1992 .

Giuseppe Piedimonte, et al., "Association of Tyrosine Protein Kinase Activity With Mitochondria in Human Fibroblasts," Journal of Cellular Biochemistry 32:113-123 (1986).

EP Search, EP Patent Application No. 04 775 923.8, dated Dec. 15, 2008.

Appleby, et al., "Murine chronic graft-versus-host disease as a model of osystemic lupus erythematosus: effect of immunosuppressive drugs on disease development," Clin. Exp. Immunol. (1989) 78, 449-453.

Bastian, et al., "Casein Interference in Bovine Plasmin Assays Using a Synthetic Substrate," (1991) J Dairy Sci 74:4119-4124.

Johnson, et al., "Mechanistic Basis for Therapeutic Targeting of the Mitochondrial FF-ATPase", downloaded from http://pubs.acs.org on Dec. 5, 2008, ASC Chem. Biol. 1 (5), 304-308, Publication Date (WEB): Jun. 9, 2006.

Adachi, M., et al., "Aberrant Transcription Caused by the Insertion an Early Transposable Element . . . ," PNAS. USA-90:1756-1760 (1993).

Adelman, N. E., et al., Treatment of (NZB X NZW)F1 Disease with Anti-I-A Monoclonal Antibodies; J. Exp. Med.-158:1350.1355 (1983).

Atwal, K.S., et al., "N-(1-Aryl-2-(1-imidazolo)ethyl)-guanidine derivates as potent inhibitors of the bovine mitochondrial F140 ATP hydrolase" Bioorganic & Medicinal Chem. Ltr., vol. 14, pp. 1021-1030 (2004).

Atwal, K.S., et al., "Small Molecule Mitochondrial F1F0 ATPase Huydrolase Inhibitors as Cardioprotective Agents" J. Med. Chem. 47, pp. 1081-1084 (2004).

Baader, S.L., et al., Uptake and Cytotoxicity of Ascorbic Acid and Dehydroascorbic Acid . . . Anticancer Research-14:221-228 (1994).

Beale, P.J., et al., "BCL-2 Family Protein Expression and Platinum Drug Resistance in Ovarian Carcinoma," British Journal of Cancer—82 (2) :436-440 (2000).

Beurdeley-Thomas, et al., "The peripheral benzodiazepine receptors: a review," Journal of Neuro-Oncology 46 (2000) 45-56.

Blatt, Neal B., "Benzodiazepine-induced superoxide signals B cell apoptosis: mechanistic insight and potential therapeutic utility", The Journal of Clinical Investigation, Oct. 2002, vol. 110, No. 8., pp. 1123-1132.

Blum, P., et al., "Stiff-Person Syndrome: An Autoimmune Disease," Movement Disorders 6(1):12-20 (1991).

Boitano, Anthony, et al., "Structure activity studies of a novel cytotoxic benzodiazepine", Bioorganic & Medicinal Chemistry Letters, Oxford, GB, vol. 13, No. 19, 2003, pp. 3327-3330.

Bono et al., "Peripheral benzodiazepine receptor agonists exhibit potent antiapoptotic activities," Biochemical and Biophysical Research Communications, 1999, 265, pp. 457-461.

Boojamra, C.G., et al., "Solid-Phase Synthesis of 1,4. Benzodiazepine-2,5-Diones. Library Prep. and Demonstration of Synthesis Generality," J. Org. Chem.-62:1240-1256 (1997).

Bunin et al., "Synthesis and evaluation of 1,4-benzodiazepine libraries", Methods in Enzymology, 1996, 267, pp. 448-465.

Bunin, B.A., et al., "The Combinatorial Synthesis and Chemical and Biological Evaluation of a 1,4-Benzodiazepine Libra ," PNAS USA-91:4708-4712 (1994).

Bunin, BA., et al., "A General and Expedient Method for the Solid-Phase Synthesis of 1,4-Benzodlazepine Derivatives," J. Am. Chem. Soc.—114:10997-10998 (1992).

Chumakov,A.M., et al., "Analysis of p53 Transactivation Through High-Affinity Bindir•g Sites," Oncogene-8:3005o3011 (1993).

Churcher et al., "A new series of potent benzodiazepine γ-Secretase inhibitors," Bioorganic & Medicinal Chemistry Letters 13 (2003) 179-.

Cohen, P.L., et al., "Lpr and gld: Single Gen• Models of Systemic Autoimmunity and Lymphoproliferative Disease," Annu. Rev. Immunol. 9:243-269 (1991).

Cole et al., "The EBV-Hybridoma Technique and its Application to Human Lung Cancer", Monoclonal Antibodies and Cancer Therapy, Alan R. Liss, Inc., pp. 77-96 [1985].

Colosi, et al,"Mutational analysis of the intracellular domain of the human growth hormone recetor", J. Biol. Chem., 268:12617 [1993].

Crabtree, R.H., "A New Type of Hydrogen Bond," Science 282:2000-2001 1998.

Darrow et al., "Structurally similar small molecule photoaffinity CCK-A Agonists and Antagonists as Novel Tools . . . ", Bioorganic & Medicinal Chemistry Letters 8 (1998) 3127-3132.

Desoize, B., "Anticancer Drug Resistance and Inhibition of Apoptosis," Anicancer Research—14:2291-2294 1994.

Dichek, David A., et al., "Seeding of intravascular stents with genetically engineered endothelial cells," Laboratory Investigation, 80:5 pp. 1347-1353 (1989).

Doble, A., et al., "Labelling of Peripheral-Type Benzodiazepine B Human Brain with [aH]l 1195: Anatomical and Subcellular Distribution," Brain Research Bulletin,18:49-61 1987.

Don, A. et al., Cancer Cell, vol. 3, May(2003) 497-509.

Donadio, J.V., et al., 'Immunosuppressive Drug Therapy in Lupus Nephritis, American Journal of Kidney Diseases 21 (3):239-250 1993.

Ermak, T.H., et al., "Treatment of Murine Lupus with Monoclonal Antibody to L3T4," Laboratory Investigation 61(4):447-456 1989.

Fuh et al, "Rational design of potent antagonists to the human growth hormone receptor", Science, 256:1677 [1992].

Gallant, J.E., et al.,"Incidence and Natural History of Cytomegalovirus Disease in Patients with Advanced Human . . . " The Journal of Infect. Disease, 166: 1223-122 (1992).

Garcia-Calvo, M., et al. "Inhibition of Human Caspases by Peptide-Based and Macromolecular Inhibitors," The Journal of Biological Chemistry 273(49):32608-32613 1998.

Gorczyca, W., et al., "Induction of DNA Slrand Breaks Associated with Apoptosis During Treatment of Leukemias," Leukemia 7(5):659-670 1993.

Gordon, C., et al.. "Chronic Therapy with Recombinant Tumor Necrosis Factor-or in Autoimmune NZB/NZW Fi Mice,"Clinical Immunology and Immunopatholoy—52:421-434 (1989).

Gordon, E.M., et al., Applications of Combinatorial Technologies to Drug Discovery. 2. Combinatorial Organic 52 Synthesis, Library Screening . . . Journal of Med. Chem. 37(10): (1994).

Grasberger, Bruce L., "Discovery and cocrystal structure of benzodiazepinedione HDM2 antagonists that activate p53 in cells", J. Med. Chem., 48, (2005), 909-912.

Karle Jesper et al., "Diazepam protects against rat hippocampal neuronal cell death induced by antisense oligodeoxynucleotide to GABA-A receptor gamma-2 subunit" Brain Research, vol. 765, No. 1, 1997, pp. 21-29.

Hahn, B.H., et al.; "Influence of Cyclophosphamide and Other Immunosuppressive Drugs on Immune Disorders . . . ," Arthritis and Rheumatism—18(2):145-152 (1975).

Hamann, L.G., et al., "Benzodiazepine-based selective inhibitors of mitochondrial F1F0 ATP hydrolase" Bioorganic & Medicinal Chemistry Ltrs. 14 pp. 1031-1034 (2004).

Hang, L., et al., "A Spontaneous Rheumatoid Arthritis-Like Disease in MR/1 Mice," J. Exp. Mod.—155:1690-1701 1982.

Herranz, R., "Cholesystokinin Antagonists: Pharmacological and Therapeutic Potential", Medicinal Research Reviews 23 (2003) 559-603.

Hirsch, et al., "PK11195, a Ligand of the Mitochondrial Benzodiazepine Receptor, Facilitates the Induction of Apoptosis and Reverses Bcl-2-Mediated Cytoprotection," Experimental Cell Research 241, 426-434 (1998).

Horowitz, R.E., et al., "Cyclophosphamide Treatment of Mouse Systemic Lupus Erythematosus," Laboratory Investigation 21 (3): 199-206 1969.

Hulme, C. J. "Improved procedure for the solution phase preparation of 1,4-benzodiazepine-2,5-dione libraries . . . ", Org. Chem., 63,(1998), 8021-8023.

Huse et al., "Generation of a Large Combinatorial Library of the Immunoglobulin Repertoire in Phage Lambda", Science, 246:1275-1281 [1989].

International Search Report and Written Opinion of PCT/US2008/057827 dated Oct. 6, 2008.

IPER and ISR for PCT/us02/31942 mailed Feb. 2, 2007.

Itoh, N., et al., "The Polypeptide Encoded by the cDNA for Human Cell Surface Antigen Fas Can Mediate Apoptosis," Cell 66:233-243 (1991).

Jones, The non-conalent interaction of pyrrolo[2,1-c][benzodiazepines-5, 11-diones with DNA, Anti-Cancer Drug Design, 5:249-264 (1990).

Kamal, A., "Synthesis of DNA-interactive Pyrrolo[2,1-c][1,4] benzodiazepines by employing polymer-supported reagents . . . ," Synlett, 14,(2004), 2533-35.

Bhagavathula, Narasimharao, et al., "7-Chloro-t-(4-hydroxyphenyl_-1-methyl-3-(naphthalen-2-ylmethyl) . . . ", J. Pharmacol & Exp Ther 324: 938-947 (2008).

Borea, "Stereochemical Features Controlling Binding and Intrinsic Activity Properties of Benzodiazepine Receptor Ligands", Molecular Pharmacology, Apr. 1987, 31 (4), pp. 334-344, p. 344, Abstract.

Mahrle, et al., Br. J. Bermatol. 1974, 91, 529-540.

Mui et al. Br. J. Dermatol. 1975, 92, 255-262.

EP Search Report dated Nov. 26, 2009, EP Patent Application No. 09003224.4.

Nadin, Alan, et al., "New Synthesis of 1,3-Dihydro-1,4-benzodiazepin-2(2H)-ones and 3-Amino-1,3-dihydro-1,4-benzodiazepin-2(2H)-ones: Pd-Catalyzed Cross-Coupling of Imidoyl Chlorides with Organoboronic Acids," J. Org. Chem., 2003, 68, pp. 2844-2852.

Reddy, Pavan, et al., "Interleukin-18 Regulates Acute Graft-Versus-Host Disease by Enhancing Fas-mediated Donor T Cell Apoptosis," J. Exp. Med., 2001, 194: 1433-1440.

Bossu, et al., "IL-18 cDNA vaccination protects mice from spontaneous lupus-like automimmune disease," PNAS 2003, 100: 14181-14186.

De Bandt, et al., "Systemic lupus erythematosus induced by antitumour necrosis factor alpha therapy: a French national survey," Arthritis Res. & Ther., 2005, 7: R545-R551.

Abunasser, et al., "Etanercept-Induced Lupus Erythematosus Presenting as a Unilateral Pleural Effusion," Chest 2008, 134: 850-853.

Busca, et al., "Recombinant human soluble tumor necrosis factor recptor fusion protein as treatment for steroid refractory graft-versus-host disease following allogeneic hematopoietic stem cell transplatation," Am. J. Hematol., 2007, 82: 45-52.

Kyungjin, Kim, Steven K. Volkkan, and Jonathan A. Ellman, Synthesis of 3-Substituted 1,4-Benzodiazepin-2-ones, J. Braz. Chem. Soc. vol. 9(4), 375-379 (1998).

Kluge, et al., "Kinetics of Inactivation of the F1F0 ATPase of Propionigenium modestum by Dicyclohexylcarbodiimide in Relationship to H+ and Na+ Concentration: Probing the Binding Site for the Coupling Ions," Biochemistry 1993, 32, 10378-10386.

Covelli, Vito, "Stress, Neuropsychiatric Disorders and Immunological Effects Exerted by Benzodiazepines," Immunopharmacology and Immunotoxicology, 20(2), 199-209 (1998).

EP Search Report dated Jun. 23, 2010, EP Patent Application No. 10 003 823.1.

EP Search Report dated Aug. 10, 2010, EP Patent Application No. 08731682.4.

Office Action Mailed Apr. 3, 2009, U.S. Appl. No. 11/176,719, filed Jul. 6, 2005.

Office Action Mailed Aug. 19, 2009, U.S. Appl. No. 11/176,719, filed, Jul. 6, 2005.

Office Action Mailed May 24, 2010, U.S. Appl. No. 11/176,719, filed Jul. 6, 2005.

Cunha, 2006, "The first bismuth(III)-catalyzed guanylation of thioureas", Tetrahedron Letters 47:6955-56.

Cunha, 2002, "Bismuth nitrate pentahydrate: a new and environmentally benign reagent for guanidylation of N-benzoylthioureas", Tetrahedron Letters 43: 49-52.

Tarpley, et al., J. Chroni Diseases (1965), 18 (abstract only).

Dourlat, et al., "Novel 1,4-benzodiazepine derivaties with antiproliferative properties on tumor cell lines," Bioorganic & Medicinal Chemistry Letters, 2007, vol. 17, Issue 9, pp. 2527-2530.

Elz et al., 1989 Eur. J. Med Chem. 259-262.

Atwal et al., Tet Lett. 30, 1989, 7313.

Johnson, K.M., et al., Chemistry & Biology, 2005, 12:486-496.

Francis, T.M., et al., "Identification of cytotoxic, T-cell-selective 1,4-benzodiazepine-2,5-diones," Bioorganic & Medicinal Chemistry Letters, Pergamon, Elsevier Science, GB, vol. 16, No. 9, May 1, 2006, pp. 2423-2427.

Akssira, M., et al., "New Routes to 1,4-benzodiazepin-2,5-diones," Tetrahedron (1994), vol. 50, No. 30, pp. 9051-9060.

Mohiuddin, G., et al., "A Versatile Synthesis of 3H-1(H), 4(H)-Benzodiazepin-2,5-diones," Indian Journal of Chenmistry, 1985, vol. 24B, pp. 905-907.

Boojamra, Constantine G., et al., "An Expedient and High-Yielding Method for the Solid-Phase Synthesis of Diverse 1,4-Benzodiazepine-2, 5-diones," Journal of Organic Chemistry, 1995, vol. 60, No. 18, pp. 5742-5743.

Keating, Thomas A., et al., "A Remarkable Two-Step Synthesis of Diverse 1, 4-Benzodiazepine-2, 5-diones Using the Ugi Four-Component Condensation," Journal of Organic Chemistry, 1996, vol. 61, No. 25, pp. 8935-8939.

Juaristi, Eusebio, et al., "Enantioselective Synthesis of α-Amino Acides from Chiral 1, 4-enzodiazepine-2, 5-diones Contianing the α-Phenethyl Group," Journal of Organic Chemistry, 1999, Mar. 26, vol. 64, No. 8, pp. 2914-2918.

Marc, Gasper, et al., "High Yield Phase Transfer N-Alkylation of Some Benzodiazepinese by Esters of ω-Halo Acids," Synthetic Communications, 1998, vol. 28, No. 7, pp. 1143-1157.

Bolli, M.H., et al., "Novel Benzo[1,4]diazepin-2-one-Derivaties as Endothelin Receptor Antagonists", Journal of Medicinal Chemistry, vol. 47, No. 11, Apr. 23, 2004, pp. 2776-2795.

* cited by examiner

| Compds | R | Ramos Cytotoxicity EC$_{50}$, μM[a] | Jurkat Cytotoxicity EC$_{50}$, μM[a] |
|---|---|---|---|
| 1 |  | 10.7 | 3.0 |
| 2 |  | 12.6 | 20.5 |
| 3 |  | 9.2 | 26.2 |
| 4 |  | >100 | >80 |
| 5 |  | >100 | >80 |
| 6 |  | 6.2 | 2.3 |
| 7 |  | 16.2 | 8.2 |
| 8 |  | 18.6 | 17.6 |
| 9 |  | 50.3 | 7.5 |
| 10 |  | 6.2 | 2.3 |
| 11 |  | 19.1 | 5.4 |

| Compds | R | Ramos Cytotoxicity IC$_{50}$, μM$^a$ | Jurkat Cytotoxicity IC$_{50}$, μM$^a$ | Selectivity |
|---|---|---|---|---|
| 12 | phenyl-C(CH$_3$) | 12.2 | 12.2 | 1.0 |
| 13 | 4-N(CH$_3$)$_2$-phenyl | 20.0 | 13.1 | 1.5 |
| 14 | 2-methylphenyl | 6.7 | 5.4 | 1.2 |
| 15 | 3-methylphenyl | 2.8 | 3.1 | 0.9 |
| 16 | 4-methylphenyl | 6.9 | 3.6 | 1.9 |
| 17 | 2-Cl-phenyl | 10.3 | 8.3 | 1.2 |
| 18 | 3-Cl-phenyl | 1.5 | 2.0 | 0.8 |
| 19 | 4-Cl-phenyl | 6.5 | 6.5 | 1.0 |
| 20 | 3-Br-phenyl | 9.2 | 4.8 | 1.9 |
| 21 | 4-Br-phenyl | >20 | 9.8 | >2 |
| 22 | 3-CF$_3$-phenyl | 4.0 | 4.5 | 0.9 |
| 23 | 4-CF$_3$-phenyl | 4.8 | 5.2 | 0.9 |
| 24 | 3-NO$_2$-phenyl | 4.2 | 1.5 | 2.8 |
| 25 | 4-NO$_2$-phenyl | 10.0 | 3.8 | 2.6 |
| 26 | 3-OH-phenyl | 4.0 | 1.5 | 2.7 |

| 27 |  | 6.0 | 1.5 | 4.0 |
| 28 |  | 31.8 | 15.1 | 2.1 |
| 29 |  | >20 | >20 | n/a |
| 30 |  | 4.0 | 0.5 | 8.0 |
| 31 |  | 3.0 | 0.5 | 6.0 |
| 32 |  | 2.0 | 0.5 | 4.0 |
| 33 |  | 4.1 | 1.5 | 2.7 |

*Values are means of three experiments, standard deviation is ± 3%.

Fig. 5

| Cmpd | R1 | R2 | R3 | R4 | Ramos EC$_{50}$ (fold change) highest[drug] % dead | Jurkat EC$_{50}$ (fold change) highest[drug] % dead | Selectivity |
|---|---|---|---|---|---|---|---|
| TMG-19 | (4-tert-butylphenyl) | Me | 7-Cl | H | 16.2 (3.2x) [25μM] = 100% | 8.2 (1.1x) [40μM] = 100% | 2.0 |
| TMG-36 | (4-iodophenyl) | Me | 7-Cl | H | 8.9 (1.8x) [40μM] =95% | 3.6 (0.5x) [40μM] = 97% | 2.5 |
| TMG-50 | (indol-3-yl) | Me | 7-Cl | H | 9 (1.8x) [100μM] = 50% | 26.2 (3.6x) [80μM] = 73% | NA |
| TMG-39 Tmf-ii-45 | (biphenyl) | Me | 7-Cl | H | 6.2 (1.2x) [18μM] = 92% | 2.3 (0.3x) [9μM] = 95% | 2.7 |

Compound core structure: benzodiazepinedione with R$_1$, R$_2$, R$_3$, R$_4$ substituents.

Fig. 5 (continued)

| | | | | | | |
|---|---|---|---|---|---|---|
| TMFI-225-20 | (3-methylsulfonyl biphenyl structure) | Me | 7-Cl | H | 8.5 (1.4) Bz = 6.0 [20µM] = 63% | 3.0 (0.5x) Bz = 6.0 [20µM] = 90% | 2.8 |
| Tmfi-294-8 | (3-NO2 biphenyl structure) | Me | 7-Cl | H | 4.2 (0.8x) Bz = 5.5 [20µM] = 83% | 1.5 (0.3x) Bz = 5.0 [20µM] = 90% | 2.8 |
| Tmfi-294-10 | (4-NO2 biphenyl structure) | Me | 7-Cl | H | 10.0 (1.8x) Bz = 5.5 [20µM] = 83% | 3.8 (0.8x) Bz = 5.0 [20µM] = 95% | 2.6 |
| TMFI-225-16 | (3-CF3 biphenyl structure) | Me | 7-Cl | H | 4.0 (0.6x) Bz = 6.5 [30µM] = 100% | 4.5 (0.56x) Bz = 8.0 [30µM] = 98% | NA |
| TMFI-225-17 | (4-CF3 biphenyl structure) | Me | 7-Cl | H | 4.8 (0.8x) Bz = 6.0 [20µM] = 100% | 5.2 (0.9x) Bz = 6.0 [20µM] = 95% | NA |

Fig. 5 (continued)

| | | | | | |
|---|---|---|---|---|---|
| TMFI-225-2 | (3-Cl biphenyl ethyl structure) | Me | 7-Cl | H | 1.5<br>(0.2x) Bz = 6.5<br>[30μM] = 100% | 2.0<br>(0.3x) Bz = 8.0<br>[20μM] = 100% | NA |
| TMFI-225-3 | (4-Cl biphenyl ethyl structure) | Me | 7-Cl | H | 6.5<br>(1.0x) Bz = 6.5<br>[30μM] = 100% | 6.5<br>(0.8x) Bz = 8.0<br>[20μM] = 100% | 1.0 |
| TMFI-225-1 | (2-Cl biphenyl ethyl structure) | Me | 7-Cl | H | 10<br>(1.7x) Bz = 6.0<br>[20μM] = 53% | 8<br>(1.3x) Bz = 6.0<br>[20μM] = 88% | 1.3 |
| Tmfi-294-19 | (3,5-diCl biphenyl structure) | Me | 7-Cl | H | 5.8<br>(0.7x) Bz = 8.0<br>[20μM] = 89% | 3.8<br>(0.6x) Bz = 6.0<br>[20μM] = 73% | 1.5 |

Fig. 5 (continued)

| | | | | | | |
|---|---|---|---|---|---|---|
| Tmfi-294-20 | (structure: 3,4-dichlorobiphenyl-CH2) | Me | 7-Cl | H | 6.5<br>(0.8x) Bz = 8.0<br>[20μM] = 90% | 7.5<br>(1.3x) Bz = 6.0<br>[20μM] = 89% | na |
| Tmfi-294-21 | (structure: 2,3-dichlorobiphenyl-CH2) | Me | 7-Cl | H | 9.0<br>(1.1x) Bz = 8.0<br>[20μM] = 68% | 7.2<br>(1.2x) Bz = 6.0<br>[20μM] = 80% | na |
| Tmfi-294-11 | (structure: 3-bromobiphenyl-CH2) | Me | 7-Cl | H | 9.2<br>(1.2x) Bz = 8.0<br>[20μM] = 68% | 4.8<br>(0.8x) Bz = 6.0<br>[20μM] = 83% | 1.9 |
| TMG-84 | (structure: 4'-methylbiphenyl-CH2CH2) | Me | 7-Cl | H | 6.9<br>(1.4x)<br>[18μM] = 96% | 3.6<br>(0.5x)<br>[8μM] = 96% | 1.9 |
| TMG-85 | (structure: 3'-methylbiphenyl-CH2CH2) | Me | 7-Cl | H | 2.8<br>(0.6x)<br>[12μM] = 96% | 3.1<br>(0.4x)<br>[8μM] = 96% | NA |

Fig. 5 (continued)

| Compound | Structure | | | | |
|---|---|---|---|---|---|
| TMG-86 | (2-methylbiphenyl-ethyl) | Me | H | 6.7 (1.3x) [15μM] = 96% | 5 (0.7x) [12μM] = 95% | 1.3 |
| TMFI-225-15 | (4-methoxybiphenyl-ethyl) | Me | 7-Cl | 4.5 (0.7x) Bz = 6.5 [30μM] = 100% | 3.0 (0.3x) Bz = 8.0 [20μM] = 98% | 1.5 |
| TMFI-225-14 | (4-hydroxybiphenyl-ethyl) | Me | 7-Cl | 6.0 (0.9x) Bz = 6.5 [30μM] = 100% | 1.5μm (0.2x) Bz = 8.0 [20μM] = 98% | 4.0 |
| TMFI-225-13 | (3-hydroxybiphenyl-ethyl) | Me | 7-Cl | 4.0 (0.6x) Bz = 6.5 [30μM] = 100% | 1.5 (0.2x) Bz = 8.0 [20μM] = 93% | 2.7 |
| TMG-76 | (pyridyl-phenyl-ethyl) | Me | H | 4.7 (0.9x) [21μM] = 81% | 0.7 (0.1x) [20μM] = 95% | 6.7 |
| TMFI-225-8 | | | | 4.0 (0.6x) Bz = 6.5 [30μM] = 100% | 0.5 (0.1x) Bz = 8.0 [20μM] = 99% | 8 |

Fig. 5 (continued)

| | | | | | |
|---|---|---|---|---|---|
| TMFI-225-9 | [3-pyridyl-phenyl structure] | Me | 7-Cl | 3.0<br>(0.5x) Bz = 6.0<br>[20µM] = 80% | 0.5<br>(0.08x) Bz = 6.0<br>[20µM] = 90% | 6 |
| 294-16 | [2-chloropyridyl-phenyl structure] | Me | 7-Cl | 7.0<br>(1.0x) Bz= 7.0<br>[20µM] = 85% | 1.5<br>(0.2x) Bz=7.0<br>[20µM] = 90% | 4.6 |
| 294-14 | [chloropyridyl-phenyl structure] | Me | 7-Cl | 9.0<br>(1.3x) Bz= 7.0<br>[20µM] = 85% | 2.0<br>(0.3x) Bz= 7.0<br>[20µM] = 90% | 4.5 |
| TMG-78 | [furan-phenyl-ethyl structure] | Me | 7-Cl | 4.5<br>(0.9x)<br>[21µM] = 89% | 1.7<br>(0.2x) | 2.6 |
| TMFI-225-7<br>Tmf-ii-46 | | | H | 2.0<br>(0.3x) Bz = 6.5<br>[20µM] = 95% | 0.5<br>(0.08x) Bz = 6.5<br>[20µM] = 100% | 4.0 |

Fig. 5 (continued)

| | | | | | |
|---|---|---|---|---|---|
| Tmfi-294-4 | [thiophene-phenyl-ethyl structure] | Me | 7-Cl | 6.2 (0.9x) Bz = 6.8 [20μM]=95% | 1.5 (0.2x) Bz = 7.5 [20μM]=98% | 4.1 |
| TMFI-225-11 | [thiophene-phenyl-ethyl structure] | Me | 7-Cl | 4.1 (0.6x) Bz = 6.5 [20μM]=100% | 1.5 (0.2x) Bz = 8.0 [20μM]=96% | 2.7 |
| Tmfi-294-22 | [methyl-thiophene-phenyl structure] | Me | 7-Cl | 6.4 (0.8x) Bz = 8.0 [30μM]=87% | 3.7 (0.6x) Bz = 6.0 [20μM]=92% | |
| Tmfi-294-24 | [Cl-thiophene-phenyl structure] | Me | 7-Cl | 7.0 (1.03x) Bz = 6.8 [20μM]=96% | 3.1 (0.4x) Bz = 7.5 [20μM]=98% | 2.25 |
| Tmf-ii-49 | [I-phenyl-S structure] | Me | H | 9.0 | 2.0 | 4.5 |
| Tmf-ii-53 | [furan-phenyl S structure] | Me | H | 5.6 | 0.85 | 6.6 |
| Tmf-ii-56 | [furan-phenyl R structure] | Me | H | 8.5 | 3.5 | 2.4 |

| | | | | | | |
|---|---|---|---|---|---|---|
| Tmf-ii-54 |  S | Me | 7-Cl | H | 5.7 | 0.7 | 8.0 |
| Tmf-ii-57 |  R | Me | 7-Cl | H | 9.0 | 0.9 | 10.0 |
| Tmf-ii-55 |  S | Me | 7-Cl | H | 3.5 | 0.5 | 7.0 |
| Tmf-ii-58 |  R | Me | 7-Cl | H | 8.2 | 1.0 | 8.2 |
| Tmf-ii-80 |  S | H | 7-Cl | H | 9.2 | 1.5 | 6.1 |
| Tmf-ii-128 |  S | H | 7-Cl | H | 2.7 | 0.5 | 5.4 |
| Tmf-ii-176 |  S | H | 7-Me | H | 2.6 | 0.75 | 3.5 |
| Tmf-ii-189 |  S | Me | 7-Me | H | 2.6 | 1.0 | 2.6 |

| | | | | | | | |
|---|---|---|---|---|---|---|---|
| Tmf-ii-95 |  | Me | 7-Br | H | 7.0 | 1.5 | 4.7 |
| Tmf-ii-218 |  | Me | 7-F | H | 1.2 | 0.3 | 4.0 |

1,4-BENZODIAZEPINE-2,5-DIONES WITH THERAPEUTIC PROPERTIES

The present application claims priority to U.S. Provisional Patent Application Ser. No. 60/732,045, filed Nov. 1, 2005, which is herein incorporated by reference in its entirety.

This invention was made with government support under AI 47450 awarded by the National Institutes of Health. The government has certain rights in the invention.

FIELD OF THE INVENTION

The present invention relates to novel chemical compounds, methods for their discovery, and their therapeutic use. In particular, the present invention provides novel 1,4-benzodiazepine-2,5-dione compounds, and methods of using novel 1,4-benzodiazepine-2,5-dione compounds as therapeutic agents to treat a number of conditions associated with the faulty regulation of the processes of programmed cell death, autoimmunity, inflammation, hyperproliferation, vascular abnormalities, cancer, anti-angiogenesis, and the like.

BACKGROUND OF THE INVENTION

Multicellular organisms exert precise control over cell number. A balance between cell proliferation and cell death achieves this homeostasis. Cell death occurs in nearly every type of vertebrate cell via necrosis or through a suicidal form of cell death, known as apoptosis. Apoptosis is triggered by a variety of extracellular and intracellular signals that engage a common, genetically programmed death mechanism.

Multicellular organisms use apoptosis to instruct damaged or unnecessary cells to destroy themselves for the good of the organism. Control of the apoptotic process therefore is very important to normal development, for example, fetal development of fingers and toes requires the controlled removal, by apoptosis, of excess interconnecting tissues, as does the formation of neural synapses within the brain. Similarly, controlled apoptosis is responsible for the sloughing off of the inner lining of the uterus (the endometrium) at the start of menstruation. While apoptosis plays an important role in tissue sculpting and normal cellular maintenance, it is also the primary defense against cells and invaders (e.g., viruses) which threaten the well being of the organism.

Not surprisingly many diseases are associated with dysregulation of the process of cell death. Experimental models have established a cause-effect relationship between aberrant apoptotic regulation and the pathenogenicity of various neoplastic, autoimmune and viral diseases. For instance, in the cell mediated immune response, effector cells (e.g., cytotoxic T lymphocytes "CTLs") destroy virus-infected cells by inducing the infected cells to undergo apoptosis. The organism subsequently relies on the apoptotic process to destroy the effector cells when they are no longer needed. Autoimmunity is normally prevented by the CTLs inducing apoptosis in each other and even in themselves. Defects in this process are associated with a variety of autoimmune diseases such as lupus erythematosus and rheumatoid arthritis.

Multicellular organisms also use apoptosis to instruct cells with damaged nucleic acids (e.g., DNA) to destroy themselves prior to becoming cancerous. Some cancer-causing viruses overcome this safeguard by reprogramming infected (transformed) cells to abort the normal apoptotic process. For example, several human papilloma viruses (HPVs) have been implicated in causing cervical cancer by suppressing the apoptotic removal of transformed cells by producing a protein (E6) which inactivates the p53 apoptosis promoter. Similarly, the Epstein-Barr virus (EBV), the causative agent of mononucleosis and Burkitt's lymphoma, reprograms infected cells to produce proteins that prevent normal apoptotic removal of the aberrant cells thus allowing the cancerous cells to proliferate and to spread throughout the organism.

Still other viruses destructively manipulate a cell's apoptotic machinery without directly resulting in the development of a cancer. For example, the destruction of the immune system in individuals infected with the human immunodeficiency virus (HIV) is thought to progress through infected $CD4^+$ T cells (about 1 in 100,000) instructing uninfected sister cells to undergo apoptosis.

Some cancers that arise by non-viral means have also developed mechanisms to escape destruction by apoptosis. Melanoma cells, for instance, avoid apoptosis by inhibiting the expression of the gene encoding Apaf-1. Other cancer cells, especially lung and colon cancer cells, secrete high levels of soluble decoy molecules that inhibit the initiation of CTL mediated clearance of aberrant cells. Faulty regulation of the apoptotic machinery has also been implicated in various degenerative conditions and vascular diseases.

It is apparent that the controlled regulation of the apoptotic process and its cellular machinery is vital to the survival of multicellular organisms. Typically, the biochemical changes that occur in a cell instructed to undergo apoptosis occur in an orderly procession. However, as shown above, flawed regulation of apoptosis can cause serious deleterious effects in the organism.

There have been various attempts to control and restore regulation of the apoptotic machinery in aberrant cells (e.g., cancer cells). For example, much work has been done to develop cytotoxic agents to destroy aberrant cells before they proliferate. As such, cytotoxic agents have widespread utility in both human and animal health and represent the first line of treatment for nearly all forms of cancer and hyperproliferative autoimmune disorders like lupus erythematosus and rheumatoid arthritis.

Many cytotoxic agents in clinical use exert their effect by damaging DNA (e.g., cis-diaminodichroplatanim(II) crosslinks DNA, whereas bleomycin induces strand cleavage). The result of this nuclear damage, if recognized by cellular factors like the p53 system, is to initiate an apoptotic cascade leading to the death of the damaged cell.

However, existing cytotoxic chemotherapeutic agents have serious drawbacks. For example, many known cytotoxic agents show little discrimination between healthy and diseased cells. This lack of specificity often results in severe side effects that can limit efficacy and/or result in early mortality. Moreover, prolonged administration of many existing cytotoxic agents results in the expression of resistance genes (e.g., bcl-2 family or multi-drug resistance (MDR) proteins) that render further dosing either less effective or useless. Some cytotoxic agents induce mutations into p53 and related proteins. Based on these considerations, ideal cytotoxic drugs should only kill diseased cells and not be susceptible to chemo-resistance.

Many autoimmune diseases and haematologic malignancies result from the aberrant survival and expansion of B and T cells in central and peripheral lymphoid organs. Current therapies for these for these disorders generally employ cytotoxic drugs whose mechanisms of action frequently involves DNA damage. Hence, the selectivity of these drugs is limited and often relies on the differential ability of diseased and healthy cells to tolerate and repair drug-induced cellular damage.

What are needed are improved compositions and methods for regulating the apoptotic processes in subjects afflicted with diseases and conditions characterized by faulty regulation of these processes (e.g., viral infections, hyperproliferative autoimmune disorders, chronic inflammatory conditions, and cancers).

SUMMARY

The present invention relates to novel chemical compounds, methods for their discovery, and their therapeutic use. In particular, the present invention provides novel 1,4-benzodiazepine-2,5-dione compounds, and methods of using novel 1,4-benzodiazepine-2,5-dione compounds as therapeutic agents to treat a number of conditions associated with the faulty regulation of the processes of programmed cell death, cancer, anti-angiogenesis, autoimmunity, inflammation, hyperproliferation, vascular abnormalities, and the like. Such compounds and uses are described throughout the present application and represent a diverse collection of compositions and applications.

Certain preferred compositions and uses are described below. The present invention is not limited to these particular compositions and uses. The present invention provides a number of useful compositions as described throughout the present application.

In certain embodiments, the present invention provides a composition comprising novel 1,4-benzodiazepine-2,5-dione compounds. In certain embodiments, the present invention provide a composition comprising a compound described by a formula selected from the group consisting of:

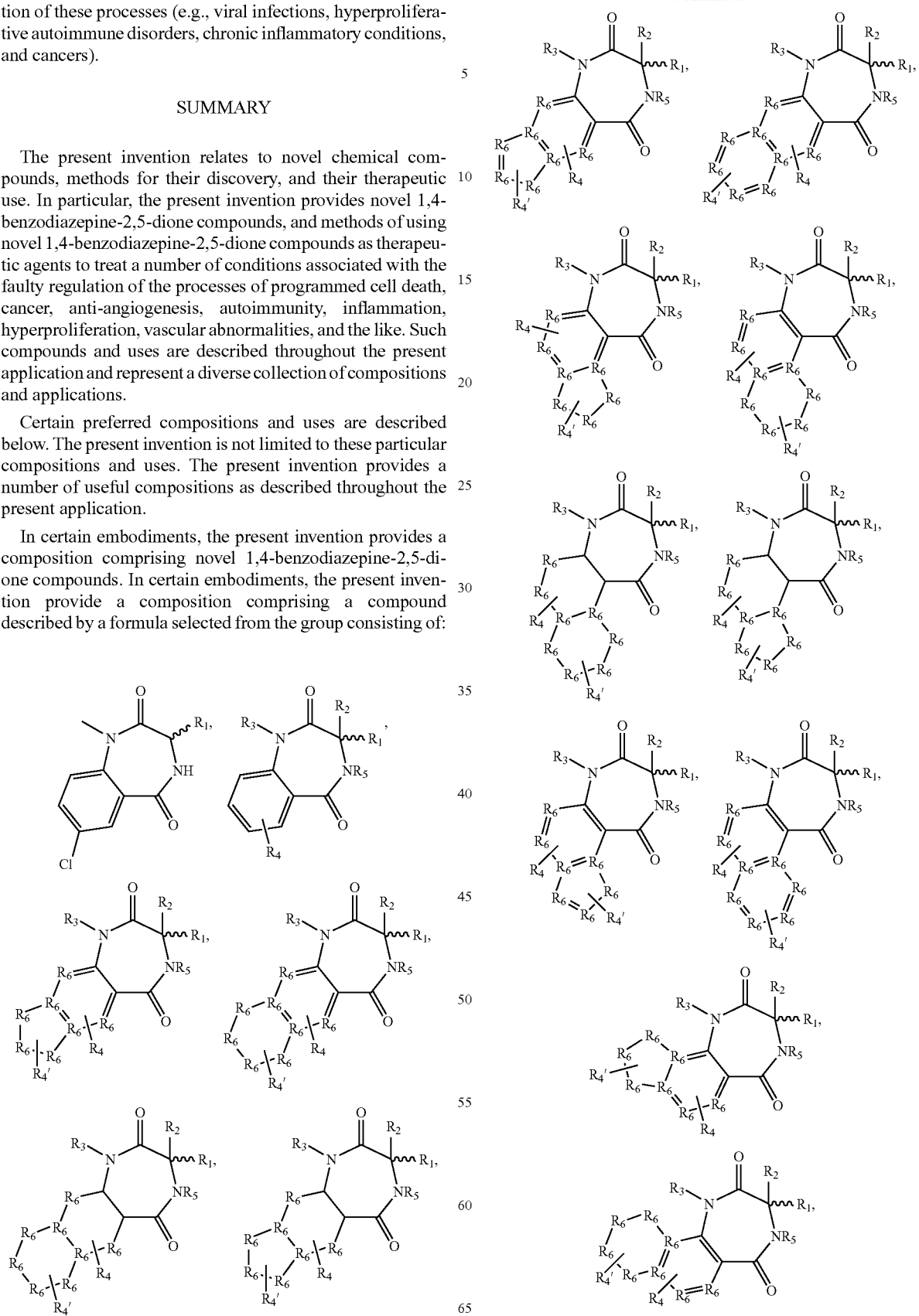

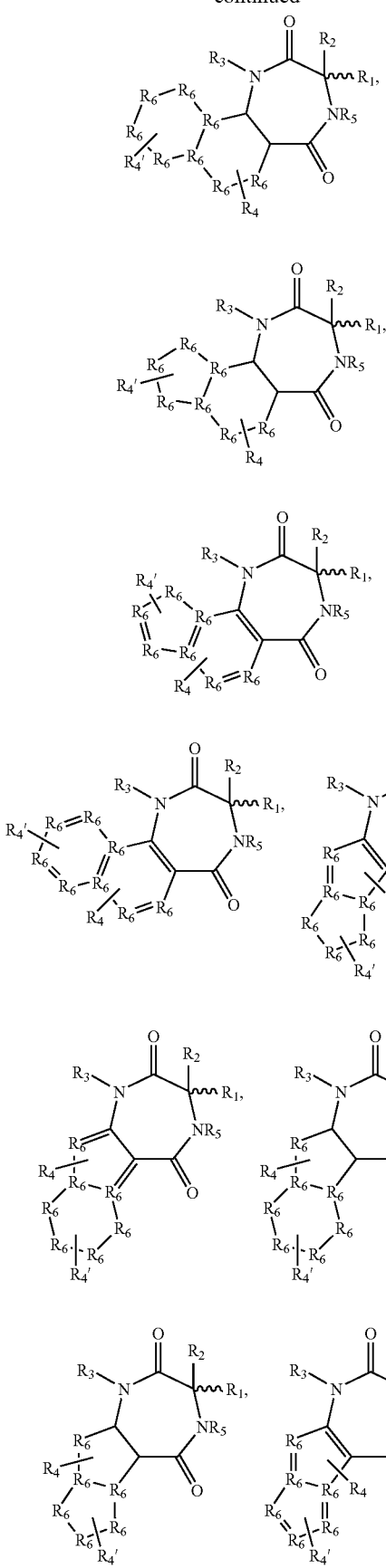

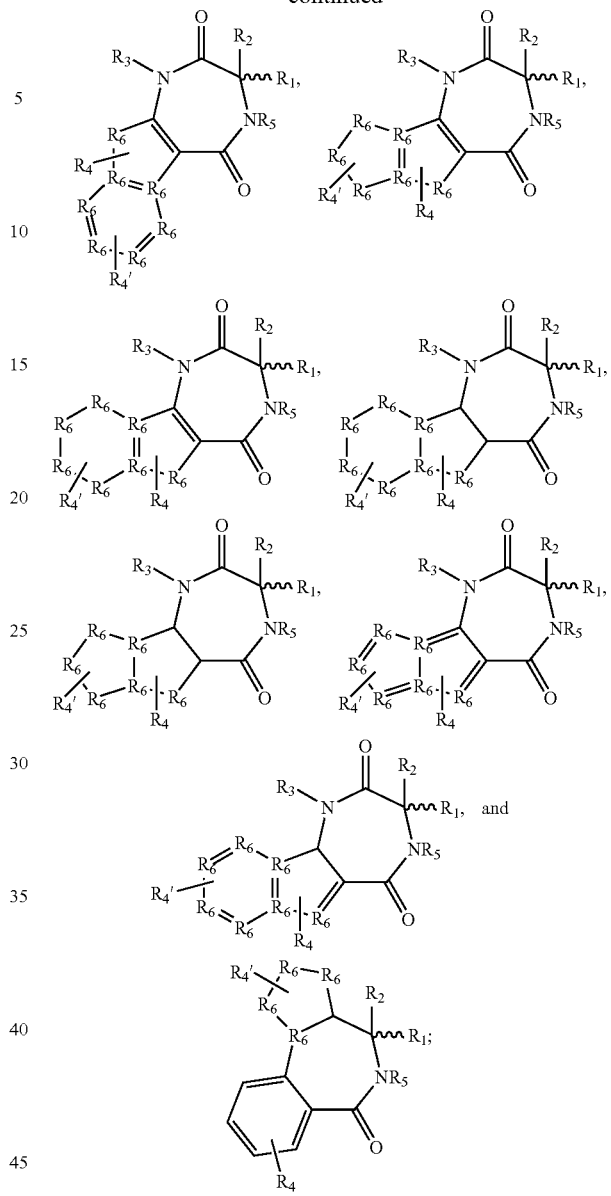

substituted and unsubstituted, including both R and S enantiomeric forms and racemic mixtures.

In some embodiments, R1 is an electron rich heterocycle. In some embodiments, the electron rich heterocycle contains 5 or more heterocyclic atoms.

In some embodiments, $R_1$ is selected from the group consisting of wherein $R_1'$ is selected from the group consisting of cycloaliphatic, aryl, substituted aryl, heterocyclic, and substituted heterocyclic.

In some embodiments, $R_2$ is selected from the group consisting of H, alkyl, substituted alkyl, and $R_1$.

In some embodiments, R₃ is selected from the group consisting of H, alkyl, and substituted alkyl.

In some embodiments, R3 is selected from the group consisting of hydrogen; halogen; OH; a chemical moiety comprising an aryl subgroup; a chemical moiety comprising a substituted aryl subgroup; a chemical moiety comprising a cycloaliphatic subgroup; a chemical moiety comprising a substituted cycloaliphatic subgroup; a chemical moiety comprising a heterocyclic subgroup; a chemical moiety comprising a substituted heterocyclic subgroup; a chemical moiety comprising at least one ester subgroup; a chemical moiety comprising at least one ether subgroup; a linear or branched, saturated or unsaturated, substituted or non-substituted, aliphatic chain having at least 2 carbons; a chemical moiety comprising Sulfur; a chemical moiety comprising Nitrogen; —OR—, wherein R is selected from the group consisting of a chemical moiety comprising an aryl subgroup; a chemical moiety comprising a substituted aryl subgroup; a chemical moiety comprising a cycloaliphatic subgroup; a chemical moiety comprising a substituted cycloaliphatic subgroup; a chemical moiety comprising a heterocyclic subgroup; a chemical moiety comprising a substituted heterocyclic subgroup; a linear or branched, saturated or unsaturated, substituted or non-substituted, aliphatic chain having at least 2 carbons; a chemical moiety comprising at least one ester subgroup; a chemical moiety comprising at least one ether subgroup; a chemical moiety comprising Sulfur; a chemical moiety comprising Nitrogen.

In some embodiments, R3 is selected from group consisting of: napthalene; phenol; 1-Napthalenol; 2-Napthalenol;

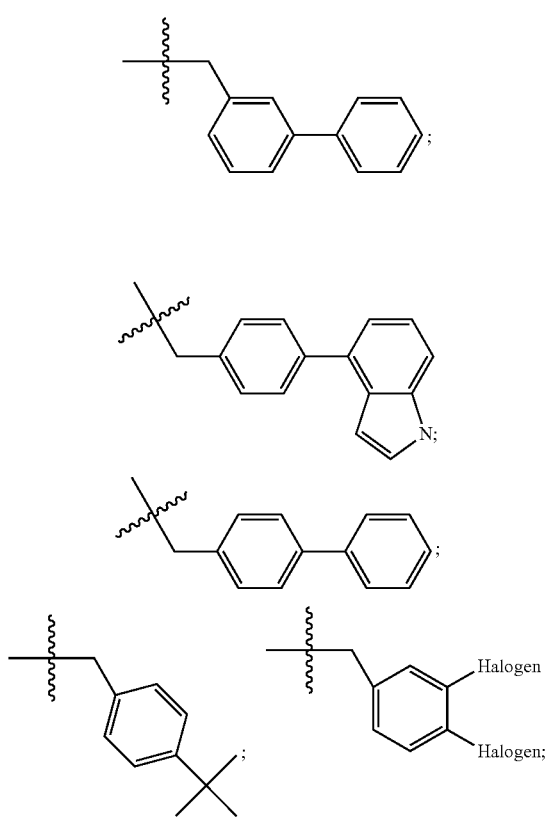

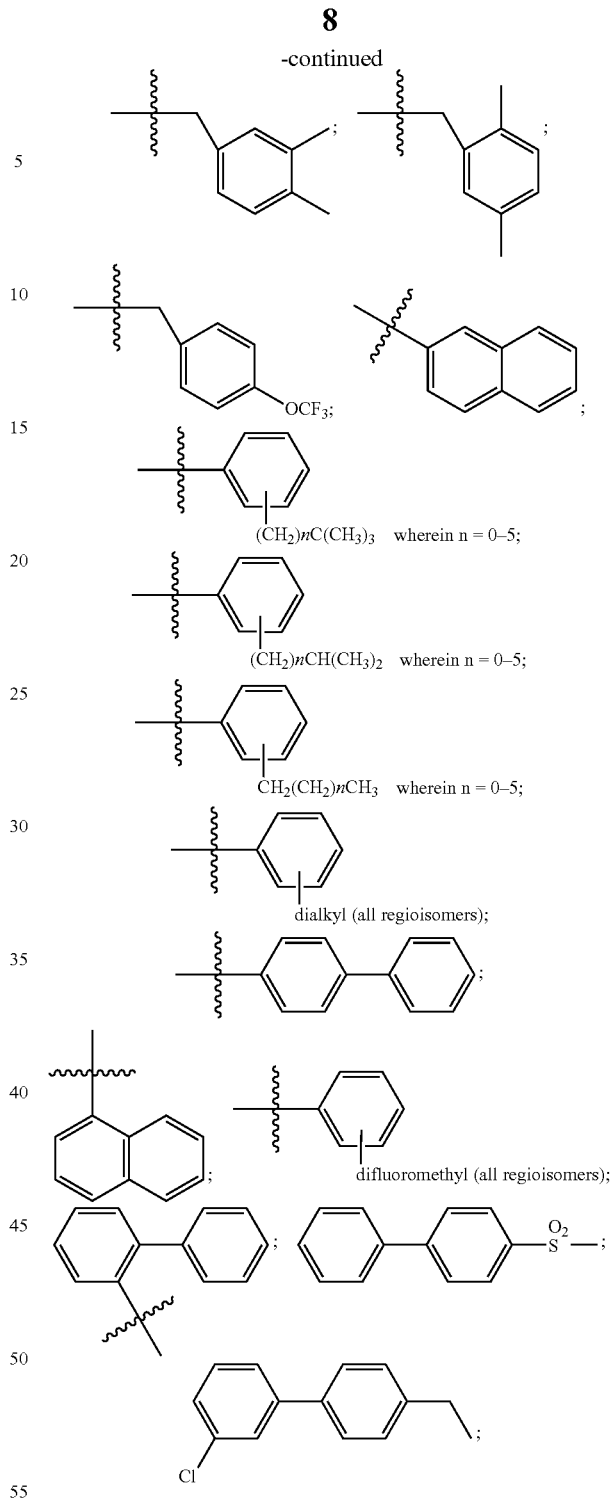

quinolines, and all aromatic regioisomers.

In some embodiments, the R1 and R3 groups may be interchanged (e.g., in some embodiments, the R1 group is positioned at the first position of the benzodiazepine ring and the R3 group is positioned at the third position of the benzodiazepine ring; in some embodiments, the R1 group is positioned at the third position of the benzodiazepine ring and the R3 group is positioned at the first position of the benzodiazepine ring).

In embodiments, $R_4$ and $R_4'$ is independently selected from the group consisting of $CH_3$, halogen, $SO_2R_4''$, SO$_2$N(R$_4$")$_2$, OR$_4$", N(R$_4$")$_2$, CON(R$_4$")$_2$, NHCOR$_4$", NHSO$_2$R4', alkyl, mono-substituted alkyl, di-substituted alkyl, tri-substituted alkyl; wherein R$_4$" is selected from the group consisting of halogen, H, alkyl, mono-substituted alkyl, di-substituted alkyl, tri-substituted alkyl, aryl, mono-substituted aryl, di-substituted aryl, tri-substituted aryl, cycloalipathic, mono-substituted cycloalipathic, di-substituted cycloalipathic, tri-substituted cycloalipathic.

In some embodiments, R$_5$ is selected from the group consisting of H, alkyl, mono-substituted aryl, di-substituted aryl, and tri-substituted aryl.

In some embodiments, R6 is selected from the group consisting of C, N or S.

In some embodiments, R1 is selected from the group consisting of:

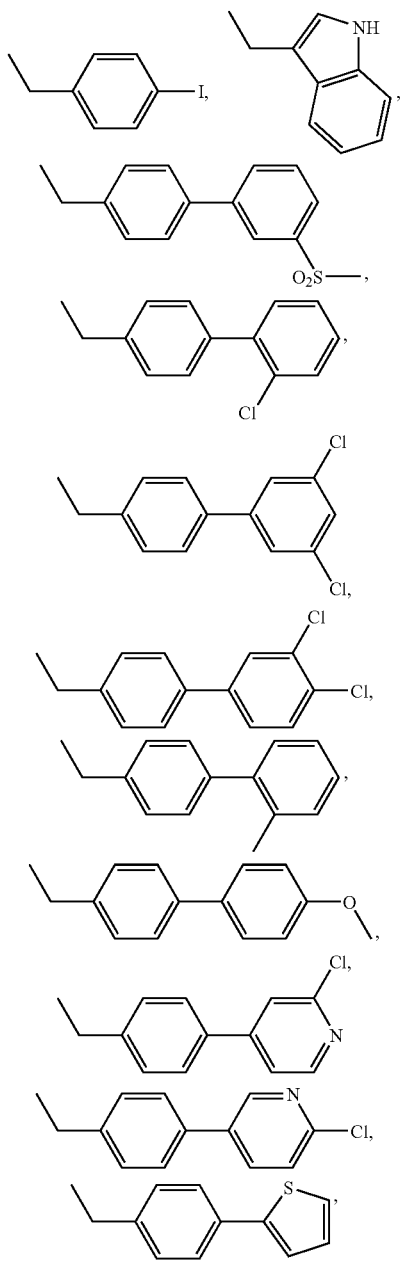

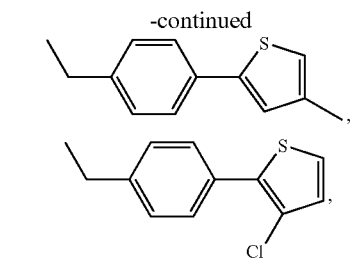

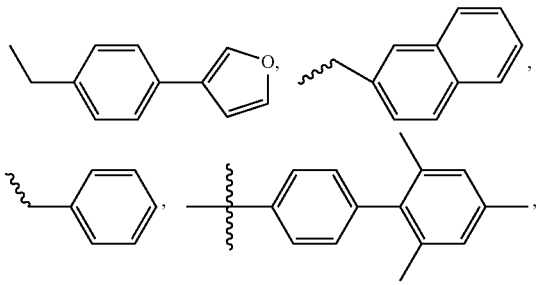

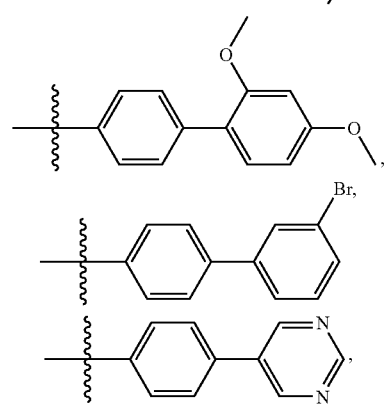

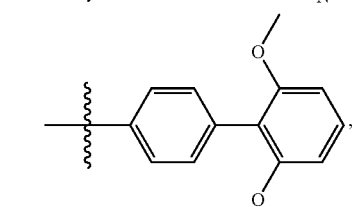

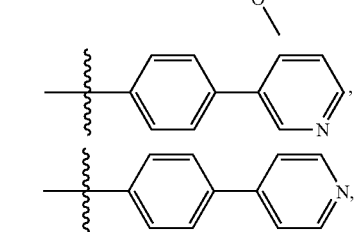

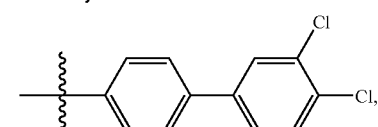

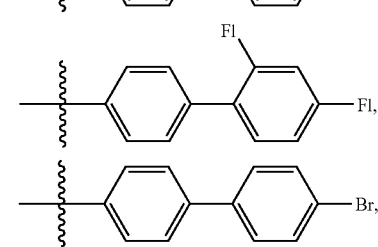

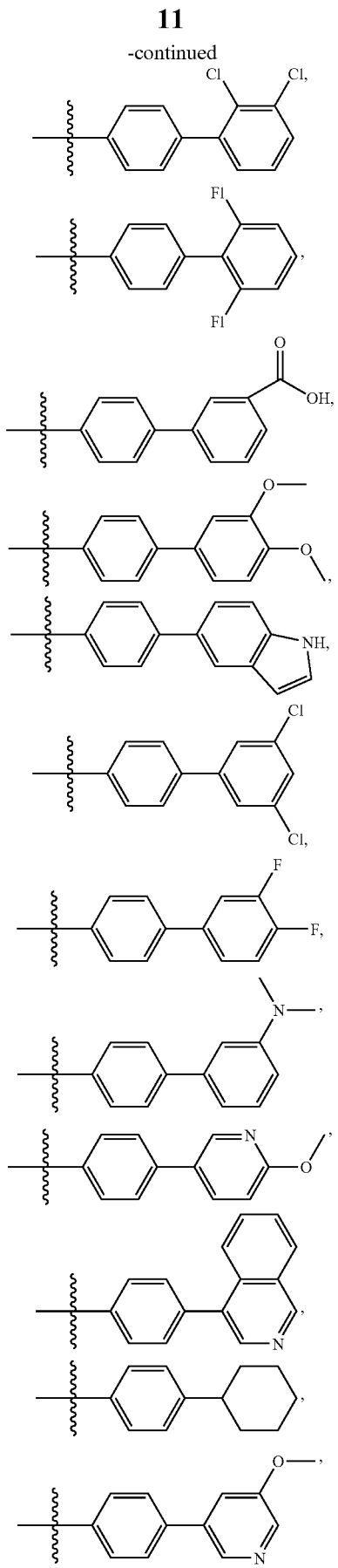
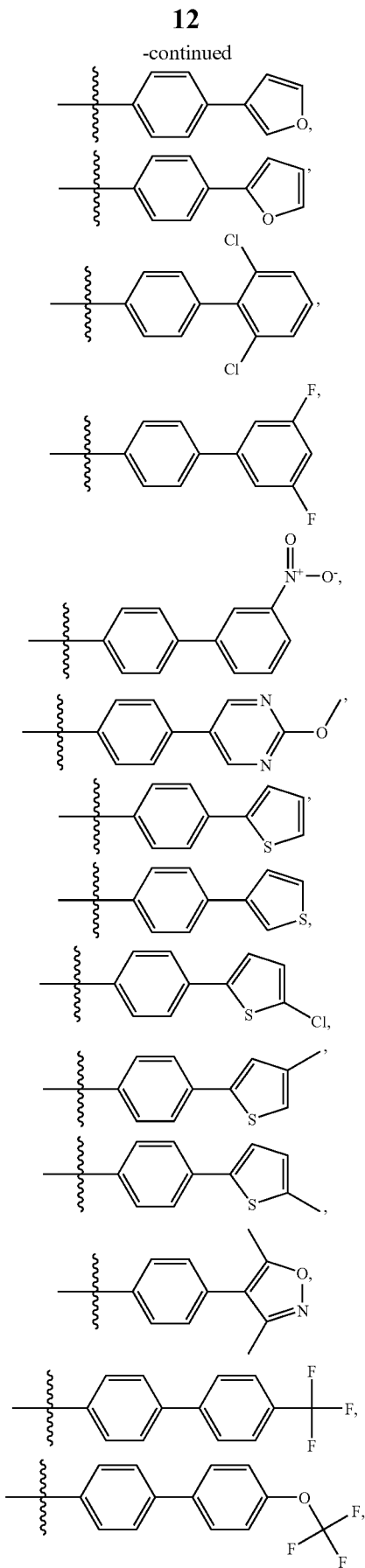

-continued
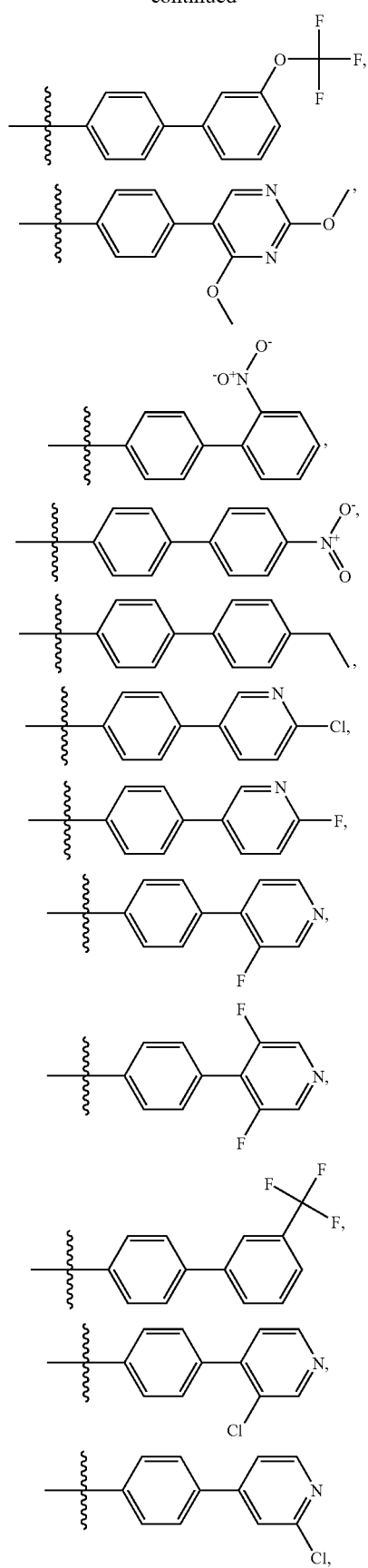
-continued
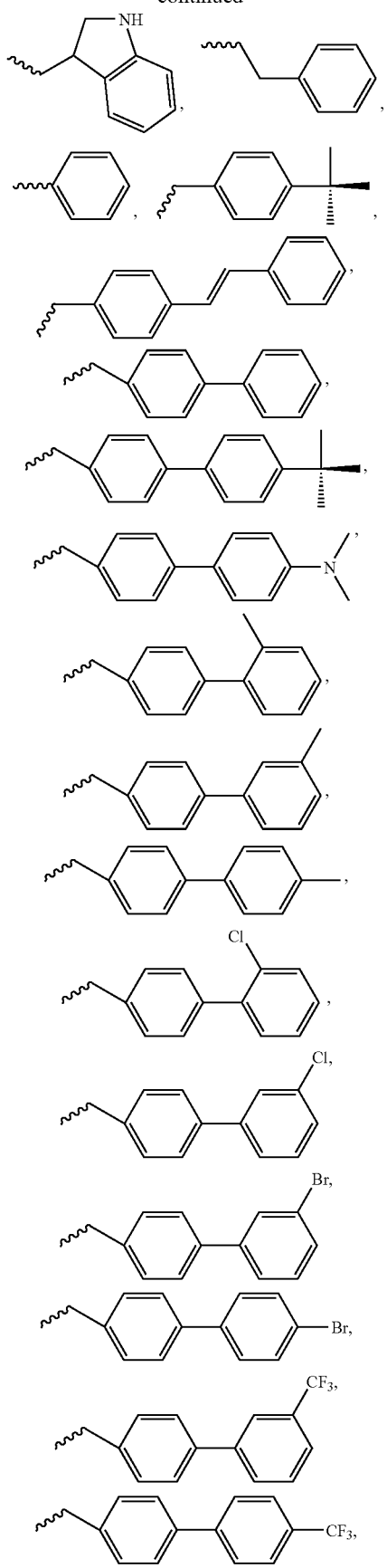

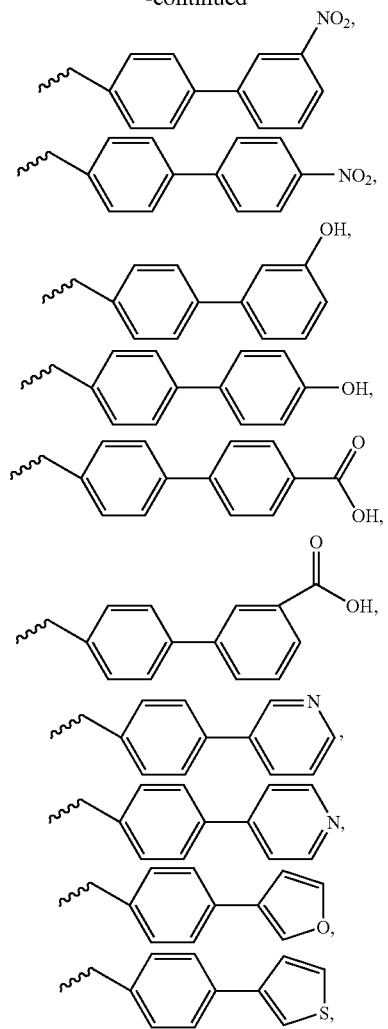
and substituted and unsubstituted, and derivatives thereof.
Certain 1,4-benzodiazepine-2,5-dione compounds of the present invention include, but are not limited to,
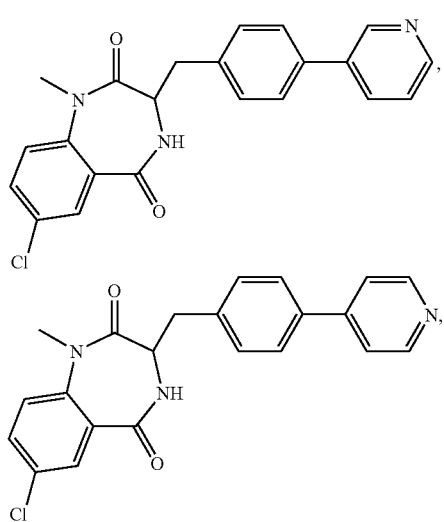
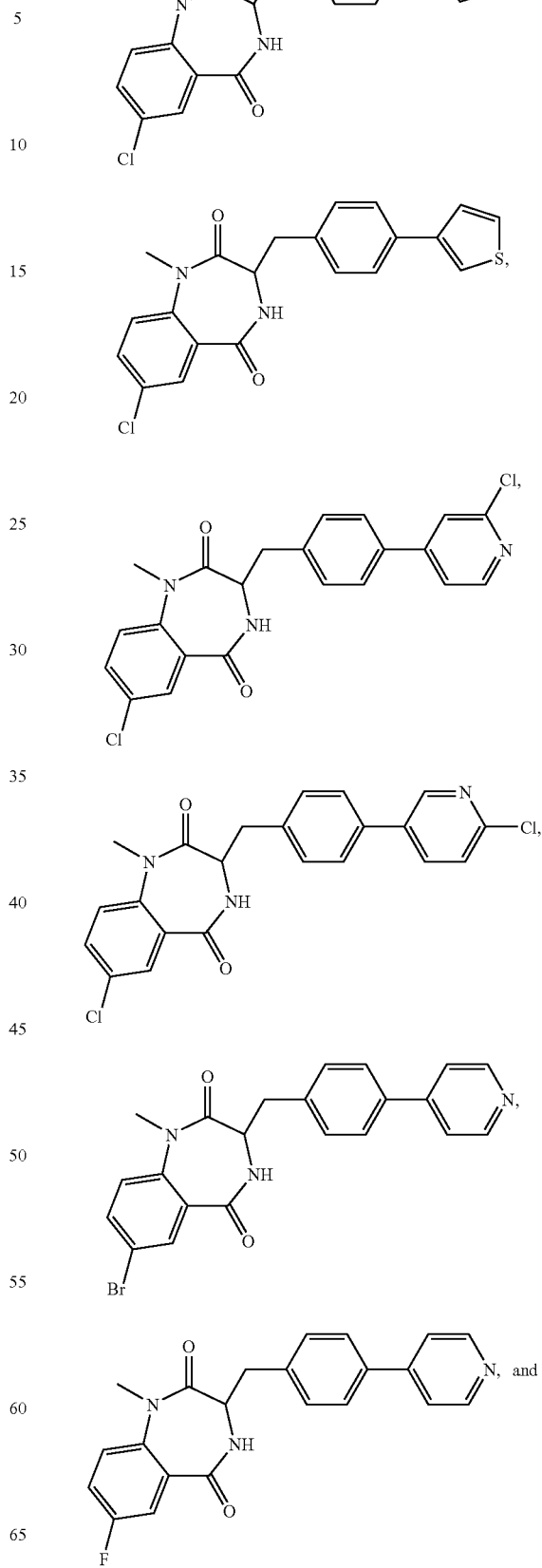

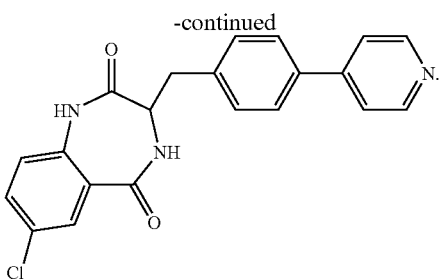

In certain embodiments, the present invention provides a method of treating cells, comprising a) providing i) target cells; and ii) a composition comprising a 1,4-benzodiazepine-2,5-dione compound having an electron rich heterocycle at the third carbon position of the benzodiazepine structure; and b) exposing the target cells to the composition under conditions such that said composition interacts with the target cell so as to induce cellular apoptosis. Such methods find use in research, drug screening, and therapeutic applications.

In some embodiments, the target cells are in a subject having, for example, an autoimmune disorder, a haematologic malignancy, or a hyproliferative disorder. In some embodiments, the target cells are selected from the group consisting of in vitro cells, in vivo cells, and ex vivo cells. In other embodiments, the target cells are cancer cells. In still other embodiments, the target cells are selected from the group consisting of B cells, T cells, and granulocytes.

DEFINITIONS

Figure 1:
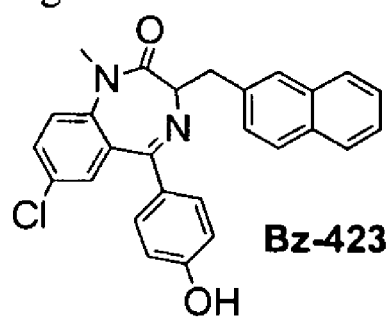
FIG. 1 shows the structure of Bz-423 and an exemplary 1,4-benzodiazepine-2,5-dione.
Figure 1:
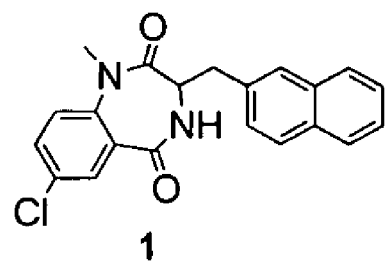

To facilitate an understanding of the present invention, a number of terms and phrases are defined below.

As used herein, the term "benzodiazepine" refers to a seven membered non-aromatic heterocyclic ring fused to a phenyl ring wherein the seven-membered ring has two nitrogen atoms, as part of the heterocyclic ring. In some aspects, the two nitrogen atoms are in the 1 and 4 positions or the 1 and 5 positions, as shown in the general structures below:

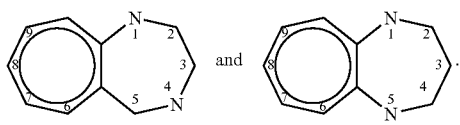

The term "larger than benzene" refers to any chemical group containing 7 or more non-hydrogen atoms.

The term "chemical moiety" refers to any chemical compound containing at least one carbon atom. Examples of chemical moieties include, but are not limited to, aromatic chemical moieties, chemical moieties comprising Sulfur, chemical moieties comprising Nitrogen, hydrophilic chemical moieties, and hydrophobic chemical moieties.

As used herein, the term "aliphatic" represents the groups including, but not limited to, alkyl, alkenyl, alkynyl, and acyclic.

As used herein, the term "aryl" represents a single aromatic ring such as a phenyl ring, or two or more aromatic rings (e.g., biphenyl, naphthalene, anthracene), or an aromatic ring and one or more non-aromatic rings. The aryl group can be optionally substituted with a lower aliphatic group (e.g., alkyl, alkenyl, alkynyl, or acyclic). Additionally, the aliphatic and aryl groups can be further substituted by one or more functional groups including, but not limited to, chemical moieties comprising N, S, O, —NH$_2$, —NHCOCH$_3$, —OH, lower alkoxy (C$_1$-C$_4$), and halo (—F, —Cl, —Br, or —I).

As used herein, the term "substituted aliphatic" refers to an alkane, alkene, alkyne, or alcyclic moiety where at least one of the aliphatic hydrogen atoms has been replaced by, for example, a halogen, an amino, a hydroxy, an ether, a nitro, a thio, a ketone, a sulfone, a sulfonamide, an aldehyde, an ester, an amide, a lower aliphatic, a substituted lower aliphatic, or a ring (aryl, substituted aryl, cycloaliphatic, or substituted cycloaliphatic, etc.). Examples of such include, but are not limited to, 1-chloroethyl and the like.

As used herein, the term "substituted aryl" refers to an aromatic ring or fused aromatic ring system consisting of at least one aromatic ring, and where at least one of the hydrogen atoms on a ring carbon has been replaced by, for example, a halogen, an amino, a hydroxy, a nitro, a thio, a ketone, an aldehyde, an ether, an ester, an amide, a sulfone, a sulfonamide, a lower aliphatic, a substituted lower aliphatic, or a ring (aryl, substituted aryl, cycloaliphatic, or substituted cycloaliphatic). Examples of such include, but are not limited to, hydroxyphenyl and the like.

As used herein, the term "cycloaliphatic" refers to an aliphatic structure containing a fused ring system. Examples of such include, but are not limited to, decalin and the like.

As used herein, the term "substituted cycloaliphatic" refers to a cycloaliphatic structure where at least one of the aliphatic hydrogen atoms has been replaced by a halogen, a heteroatom, a nitro, a thio, an amino, a hydroxy, a ketone, an aldehyde, an ester, an amide, a lower aliphatic, a substituted lower aliphatic, or a ring (aryl, substituted aryl, cycloaliphatic, or substituted cycloaliphatic). Examples of such include, but are not limited to, 1-chlorodecalyl, bicyclo-heptanes, octanes, and nonanes (e.g., nonrbornyl) and the like.

As used herein, the term "heterocyclic" represents, for example, an aromatic or nonaromatic ring containing one or more heteroatoms. The heteroatoms can be the same or different from each other. Examples of heteroatoms include, but are not limited to nitrogen, oxygen and sulfur. Aromatic and nonaromatic heterocyclic rings are well-known in the art. Some nonlimiting examples of aromatic heterocyclic rings include pyridine, pyrimidine, indole, purine, quinoline and isoquinoline. Nonlimiting examples of nonaromatic heterocyclic compounds include piperidine, piperazine, morpholine, pyrrolidine and pyrazolidine. Examples of oxygen containing heterocyclic rings include, but not limited to furan, oxirane, 2H-pyran, 4H-pyran, 2H-chromene, and benzofuran. Examples of sulfur-containing heterocyclic rings include, but are not limited to, thiophene, benzothiophene, and parathiazine. Examples of nitrogen containing rings include, but are not limited to, pyrrole, pyrrolidine, pyrazole, pyrazolidine, imidazole, imidazoline, imidazolidine, pyridine, piperidine, pyrazine, piperazine, pyrimidine, indole, purine, benzimidazole, quinoline, isoquinoline, triazole, and triazine. Nonlimiting examples of heterocyclic rings containing two different heteroatoms include, but are not limited to, phenothiazine, morpholine, parathiazine, oxazine, oxazole, thiazine, and thiazole. The heterocyclic ring is optionally further substituted with one or more groups selected from aliphatic, nitro, acetyl (i.e., —C(=O)—CH$_3$), or aryl groups.

As used herein, the term "substituted heterocyclic" refers to a heterocylic structure where at least one of the ring hydrogen atoms is replaced by oxygen, nitrogen or sulfur, and where at least one of the aliphatic hydrogen atoms has been replaced by a halogen, hydroxy, a thio, nitro, an amino, an ether, a sulfone, a sulphonamide, a ketone, an aldehyde, an ester, an amide, a lower aliphatic, a substituted lower aliphatic, or a ring (aryl, substituted aryl, cycloaliphatic, or substituted cycloaliphatic). Examples of such include, but are not limited to 2-chloropyranyl.

As used herein, the term "electron-rich heterocycle," means cyclic compounds in which one or more ring atoms is a heteroatom (e.g., oxygen, nitrogen or sulfur), and the heteroatom has unpaired electrons which contribute to a 6-π electronic system. Exemplary electron-rich heterocycles include, but are not limited to, pyrrole, indole, furan, benzofuran, thiophene, benzothiophene and other similar structures.

As used herein, the term "linker" refers to a chain containing up to and including eight contiguous atoms connecting two different structural moieties where such atoms are, for example, carbon, nitrogen, oxygen, or sulfur. Ethylene glycol is one non-limiting example.

As used herein, the term "lower-alkyl-substituted-amino" refers to any alkyl unit containing up to and including eight carbon atoms where one of the aliphatic hydrogen atoms is replaced by an amino group. Examples of such include, but are not limited to, ethylamino and the like.

As used herein, the term "lower-alkyl-substituted-halogen" refers to any alkyl chain containing up to and including eight carbon atoms where one of the aliphatic hydrogen atoms is replaced by a halogen. Examples of such include, but are not limited to, chlorethyl and the like.

As used herein, the term "acetylamino" shall mean any primary or secondary amino that is acetylated. Examples of such include, but are not limited to, acetamide and the like.

As used herein, the term "a moiety that participates in hydrogen bonding" as used herein represents a group that can accept or donate a proton to form a hydrogen bond thereby. Some specific non-limiting examples of moieties that participate in hydrogen bonding include a fluoro, oxygen-containing and nitrogen-containing groups that are well-known in the art. Some examples of oxygen-containing groups that participate in hydrogen bonding include: hydroxy, lower alkoxy, lower carbonyl, lower carboxyl, lower ethers and phenolic groups. The qualifier "lower" as used herein refers to lower aliphatic groups ($C_1$-$C_4$) to which the respective oxygen-containing functional group is attached. Thus, for example, the term "lower carbonyl" refers to inter alia, formaldehyde, acetaldehyde. Some nonlimiting examples of nitrogen-containing groups that participate in hydrogen bond formation include amino and amido groups. Additionally, groups containing both an oxygen and a nitrogen atom can also participate in hydrogen bond formation. Examples of such groups include nitro, N-hydroxy and nitrous groups. It is also possible that the hydrogen-bond acceptor in the present invention can be the π electrons of an aromatic ring.

The term "derivative" of a compound, as used herein, refers to a chemically modified compound wherein the chemical modification takes place either at a functional group of the compound (e.g., aromatic ring) or benzodiazepine backbone. Such derivatives include, but are not limited to, esters of alcohol-containing compounds, esters of carboxy-containing compounds, amides of amine-containing compounds, amides of carboxy-containing compounds, imines of amino-containing compounds, acetals of aldehyde-containing compounds, ketals of carbonyl-containing compounds, and the like.

As used herein, the term "subject" refers to organisms to be treated by the methods of the present invention. Such organisms preferably include, but are not limited to, mammals (e.g., murines, simians, equines, bovines, porcines, canines, felines, and the like), and most preferably includes humans. In the context of the invention, the term "subject" generally refers to an individual who will receive or who has received treatment (e.g., administration of a compound of the present invention and optionally one or more other agents) for a condition characterized by the dysregulation of apoptotic processes.

The term "diagnosed," as used herein, refers to the to recognition of a disease by its signs and symptoms (e.g., resistance to conventional therapies), or genetic analysis, pathological analysis, histological analysis, and the like.

As used herein, the terms "anticancer agent," or "conventional anticancer agent" refer to any chemotherapeutic compounds, radiation therapies, or surgical interventions, used in the treatment of cancer.

As used herein the term, "in vitro" refers to an artificial environment and to processes or reactions that occur within an artificial environment. In vitro environments include, but are not limited to, test tubes and cell cultures. The term "in vivo" refers to the natural environment (e.g., an animal or a cell) and to processes or reaction that occur within a natural environment.

As used herein, the term "host cell" refers to any eukaryotic or prokaryotic cell (e.g., mammalian cells, avian cells, amphibian cells, plant cells, fish cells, and insect cells), whether located in vitro or in vivo.

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro, including oocytes and embryos.

In preferred embodiments, the "target cells" of the compositions and methods of the present invention include, refer to, but are not limited to, lymphoid cells or cancer cells. Lymphoid cells include B cells, T cells, granulocytes, dendritic cells, and antigen presenting cells. Granulocytes include eosinophils and macrophages. In some embodiments, target cells are continuously cultured cells or uncultured cells obtained from patient biopsies.

Cancer cells include tumor cells, neoplastic cells, malignant cells, metastatic cells, and hyperplastic cells. Neoplastic cells can be benign or malignant. Neoplastic cells are benign if they do not invade or metastasize. A malignant cell is one that is able to invade and/or metastasize. Hyperplasia is a pathologic accumulation of cells in a tissue or organ, without significant alteration in structure or function.

In one specific embodiment, the target cells exhibit pathological growth or proliferation. As used herein, the term "pathologically proliferating or growing cells" refers to a localized population of proliferating cells in an animal that is not governed by the usual limitations of normal growth.

As used herein, the term "un-activated target cell" refers to a cell that is either in the $G_o$ phase or one in which a stimulus has not been applied.

As used herein, the term "activated target lymphoid cell" refers to a lymphoid cell that has been primed with an appropriate stimulus to cause a signal transduction cascade, or alternatively, a lymphoid cell that is not in $G_o$ phase. Activated lymphoid cells may proliferate, undergo activation induced cell death, or produce one or more of cytotoxins, cytokines, and other related membrane-associated proteins characteristic of the cell type (e.g., $CD8^+$ or $CD4^+$). They are also capable of recognizing and binding any target cell that displays a particular antigen on its surface, and subsequently releasing its effector molecules.

As used herein, the term "activated cancer cell" refers to a cancer cell that has been primed with an appropriate stimulus to cause a signal transduction. An activated cancer cell may or may not be in the $G_0$ phase.

An activating agent is a stimulus that upon interaction with a target cell results in a signal transduction cascade. Examples of activating stimuli include, but are not limited to, small molecules, radiant energy, and molecules that bind to cell activation cell surface receptors. Responses induced by activation stimuli can be characterized by changes in, among others, intracellular $Ca^{2+}$, hydroxyl radical levels; the activity of enzymes like kinases or phosphatases; or the energy state of the cell. For cancer cells, activating agents also include transforming oncogenes.

As used herein, the term "effective amount" refers to the amount of a compound (e.g., a compound of the present invention) sufficient to effect beneficial or desired results. An effective amount can be administered in one or more administrations, applications or dosages and is not limited intended to be limited to a particular formulation or administration route.

As used herein, the term "dysregulation of the process of cell death" refers to any aberration in the ability of (e.g., predisposition) a cell to undergo cell death via either necrosis or apoptosis. Dysregulation of cell death is associated with or induced by a variety of conditions, including for example, autoimmune disorders (e.g., systemic lupus erythematosus, rheumatoid arthritis, myasthenia gravis, Sjögren's syndrome, etc.), chronic inflammatory conditions (e.g., graft-versus-host disease, psoriasis, asthma and Crohn's disease), hyperproliferative disorders (e.g., tumors, B cell lymphomas, T cell lymphomas, etc.), viral infections (e.g., herpes, papilloma, HIV), and other conditions such as osteoarthritis and atherosclerosis.

It should be noted that when the dysregulation is induced by or associated with a viral infection, the viral infection may or may not be detectable at the time dysregulation occurs or is observed. That is, viral-induced dysregulation can occur even after the disappearance of symptoms of viral infection.

A "hyperproliferative disorder," as used herein refers to any condition in which a localized population of proliferating cells in an animal is not governed by the usual limitations of normal growth. Examples of hyperproliferative disorders include tumors, neoplasms, lymphomas and the like. A neoplasm is said to be benign if it does not undergo, invasion or metastasis and malignant if it does either of these. A metastatic cell or tissue means that the cell can invade and destroy neighboring body structures. Hyperplasia is a form of cell proliferation involving an increase in cell number in a tissue or organ, without significant alteration in structure or function. Metaplasia is a form of controlled cell growth in which one type of fully differentiated cell substitutes for another type of differentiated cell. Metaplasia can occur in epithelial or connective tissue cells. A typical metaplasia involves a somewhat disorderly metaplastic epithelium.

The pathological growth of activated lymphoid cells often results in an autoimmune disorder or a chronic inflammatory condition. As used herein, the term "autoimmune disorder" refers to any condition in which an organism produces antibodies or immune cells which recognize the organism's own molecules, cells or tissues. Non-limiting examples of autoimmune disorders include autoimmune hemolytic anemia, autoimmune hepatitis, Berger's disease or IgA nephropathy, Celiac Sprue, chronic fatigue syndrome, Crohn's disease, dermatomyositis, fibromyalgia, graft versus host disease, Grave's disease, Hashimoto's thyroiditis, idiopathic thrombocytopenia purpura, lichen planus, multiple sclerosis, myasthenia gravis, psoriasis, rheumatic fever, rheumatic arthritis, scleroderma, Sjorgren syndrome, systemic lupus erythematosus, type 1 diabetes, ulcerative colitis, vitiligo, tuberculosis, and the like.

As used herein, the term "chronic inflammatory condition" refers to a condition wherein the organism's immune cells are activated. Such a condition is characterized by a persistent inflammatory response with pathologic sequalae. This state is characterized by infiltration of mononuclear cells, proliferation of fibroblasts and small blood vessels, increased connective tissue, and tissue destruction. Examples of chronic inflammatory diseases include, but are not limited to, Crohn's disease, psoriasis, chronic obstructive pulmonary disease, inflammatory bowel disease, multiple sclerosis, and asthma. Autoimmune diseases such as rheumatoid arthritis and systemic lupus erythematosus can also result in a chronic inflammatory state.

As used herein, the term "co-administration" refers to the administration of at least two agent(s) (e.g., a compound of the present invention) or therapies to a subject. In some embodiments, the co-administration of two or more agents/therapies is concurrent. In other embodiments, a first agent/therapy is administered prior to a second agent/therapy. Those of skill in the art understand that the formulations and/or routes of administration of the various agents/therapies used may vary. The appropriate dosage for co-administration can be readily determined by one skilled in the art. In some embodiments, when agents/therapies are co-administered, the respective agents/therapies are administered at lower dosages than appropriate for their administration alone. Thus, co-administration is especially desirable in embodiments where the co-administration of the agents/therapies lowers the requisite dosage of a known potentially harmful (e.g., toxic) agent(s).

As used herein, the term "toxic" refers to any detrimental or harmful effects on a cell or tissue as compared to the same cell or tissue prior to the administration of the toxicant.

As used herein, the term "pharmaceutical composition" refers to the combination of an active agent with a carrier, inert or active, making the composition especially suitable for diagnostic or therapeutic use in vivo, in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants. (See e.g., Martin, Remington's Pharmaceutical Sciences, 15th Ed., Mack Publ. Co., Easton, Pa. [1975]).

As used herein, the term "pharmaceutically acceptable salt" refers to any pharmaceutically acceptable salt (e.g., acid or base) of a compound of the present invention which, upon administration to a subject, is capable of providing a compound of this invention or an active metabolite or residue thereof. As is known to those of skill in the art, "salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metals (e.g., sodium) hydroxides, alkaline earth metals (e.g., magnesium), hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

As used herein, the term "pathogen" refers a biological agent that causes a disease state (e.g., infection, cancer, etc.) in a host. "Pathogens" include, but are not limited to, viruses, bacteria, archaea, fungi, protozoans, mycoplasma, prions, and parasitic organisms.

The terms "bacteria" and "bacterium" refer to all prokaryotic organisms, including those within all of the phyla in the Kingdom Procaryotae. It is intended that the term encompass all microorganisms considered to be bacteria including Mycoplasma, Chlamydia, Actinomyces, Streptomyces, and Rickettsia. All forms of bacteria are included within this definition including cocci, bacilli, spirochetes, spheroplasts, protoplasts, etc. Also included within this term are prokaryotic organisms which are gram negative or gram positive. "Gram negative" and "gram positive" refer to staining patterns with the Gram-staining process which is well known in the art. (See e.g., Finegold and Martin, Diagnostic Microbiology, 6th Ed., CV Mosby St. Louis, pp. 13-15 [1982]). "Gram positive bacteria" are bacteria which retain the primary dye used in the Gram stain, causing the stained cells to appear dark blue to purple under the microscope. "Gram negative bacteria" do not retain the primary dye used in the Gram stain, but are stained by the counterstain. Thus, gram negative bacteria appear red.

As used herein, the term "microorganism" refers to any species or type of microorganism, including but not limited to, bacteria, archaea, fungi, protozoans, mycoplasma, and parasitic organisms. The present invention contemplates that a number of microorganisms encompassed therein will also be pathogenic to a subject.

As used herein, the term "fungi" is used in reference to eukaryotic organisms such as the molds and yeasts, including dimorphic fungi.

As used herein, the term "virus" refers to minute infectious agents, which with certain exceptions, are not observable by light microscopy, lack independent metabolism, and are able to replicate only within a living host cell. The individual particles (i.e., virions) typically consist of nucleic acid and a protein shell or coat; some virions also have a lipid containing membrane. The term "virus" encompasses all types of viruses, including animal, plant, phage, and other viruses.

The term "sample" as used herein is used in its broadest sense. A sample suspected of indicating a condition characterized by the dysregulation of apoptotic function may comprise a cell, tissue, or fluids, chromosomes isolated from a cell (e.g., a spread of metaphase chromosomes), genomic DNA (in solution or bound to a solid support such as for Southern blot analysis), RNA (in solution or bound to a solid support such as for Northern blot analysis), cDNA (in solution or bound to a solid support) and the like. A sample suspected of containing a protein may comprise a cell, a portion of a tissue, an extract containing one or more proteins and the like.

As used herein, the terms "purified" or "to purify" refer, to the removal of undesired components from a sample. As used herein, the term "substantially purified" refers to molecules that are at least 60% free, preferably 75% free, and most preferably 90%, or more, free from other components with which they usually associated.

As used herein, the term "antigen binding protein" refers to proteins which bind to a specific antigen. "Antigen binding proteins" include, but are not limited to, immunoglobulins, including polyclonal, monoclonal, chimeric, single chain, and humanized antibodies, Fab fragments, F(ab')2 fragments, and Fab expression libraries. Various procedures known in the art are used for the production of polyclonal antibodies. For the production of antibody, various host animals can be immunized by injection with the peptide corresponding to the desired epitope including but not limited to rabbits, mice, rats, sheep, goats, etc. In a preferred embodiment, the peptide is conjugated to an immunogenic carrier (e.g., diphtheria toxoid, bovine serum albumin (BSA), or keyhole limpet hemocyanin [KLH]). Various adjuvants are used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum.*

For preparation of monoclonal antibodies, any technique that provides for the production of antibody molecules by continuous cell lines in culture may be used (See e.g., Harlow and Lane, Antibodies: A Laboratory Manual, Cold Spring Harbor Laboratory Press, Cold Spring Harbor, N.Y.). These include, but are not limited to, the hybridoma technique originally developed by Köhler and Milstein (Köhler and Milstein, Nature, 256:495-497 [1975]), as well as the trioma technique, the human B-cell hybridoma technique (See e.g., Kozbor et al., Immunol. Today, 4:72 [1983]), and the EBV-hybridoma technique to produce human monoclonal antibodies (Cole et al., in Monoclonal Antibodies and Cancer Therapy, Alan R. Liss, Inc., pp. 77-96 [1985]).

According to the invention, techniques described for the production of single chain antibodies (U.S. Pat. No. 4,946,778; herein incorporated by reference) can be adapted to produce specific single chain antibodies as desired. An additional embodiment of the invention utilizes the techniques known in the art for the construction of Fab expression libraries (Huse et al., Science, 246:1275-1281 [1989]) to allow rapid and easy identification of monoclonal Fab fragments with the desired specificity.

Antibody fragments that contain the idiotype (antigen binding region) of the antibody molecule can be generated by known techniques. For example, such fragments include but are not limited to: the F(ab')2 fragment that can be produced by pepsin digestion of an antibody molecule; the Fab' fragments that can be generated by reducing the disulfide bridges of an F(ab')2 fragment, and the Fab fragments that can be generated by treating an antibody molecule with papain and a reducing agent.

Genes encoding antigen binding proteins can be isolated by methods known in the art. In the production of antibodies, screening for the desired antibody can be accomplished by techniques known in the art (e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), Western Blots, precipitation reactions, agglutination assays (e.g., gel agglutination assays, hemagglutination assays, etc.), complement fixation assays, immunofluorescence assays, protein A assays, and immunoelectrophoresis assays, etc.) etc.

As used herein, the term "immunoglobulin" or "antibody" refer to proteins that bind a specific antigen. Immunoglobulins include, but are not limited to, polyclonal, monoclonal, chimeric, and humanized antibodies, Fab fragments, F(ab')$_2$ fragments, and includes immunoglobulins of the following classes: IgG, IgA, IgM, IgD, IbE, and secreted immunoglobulins (sIg). Immunoglobulins generally comprise two identical heavy chains and two light chains. However, the terms "antibody" and "immunoglobulin" also encompass single chain antibodies and two chain antibodies.

The term "epitope" as used herein refers to that portion of an antigen that makes contact with a particular immunoglobulin. When a protein or fragment of a protein is used to immunize a host animal, numerous regions of the protein may induce the production of antibodies which bind specifically to a given region or three-dimensional structure on the protein; these regions or structures are referred to as "antigenic determinants". An antigenic determinant may compete with the intact antigen (i.e., the "immunogen" used to elicit the immune response) for binding to an antibody.

The terms "specific binding" or "specifically binding" when used in reference to the interaction of an antibody and a protein or peptide means that the interaction is dependent upon the presence of a particular structure (i.e., the antigenic determinant or epitope) on the protein; in other words the antibody is recognizing and binding to a specific protein structure rather than to proteins in general. For example, if an antibody is specific for epitope "A," the presence of a protein containing epitope A (or free, unlabelled A) in a reaction containing labeled "A" and the antibody will reduce the amount of labeled A bound to the antibody.

As used herein, the terms "non-specific binding" and "background binding" when used in reference to the interaction of an antibody and a protein or peptide refer to an interaction that is not dependent on the presence of a particular structure (i.e., the antibody is binding to proteins in general rather that a particular structure such as an epitope).

As used herein, the term "modulate" refers to the activity of a compound (e.g., a compound of the present invention) to affect (e.g., to promote or retard) an aspect of cellular function, including, but not limited to, cell growth, proliferation, apoptosis, and the like.

The term "test compound" refers to any chemical entity, pharmaceutical, drug, and the like, that can be used to treat or prevent a disease, illness, sickness, or disorder of bodily function, or otherwise alter the physiological or cellular status of a sample (e.g., the level of dysregulation of apoptosis in a cell or tissue). Test compounds comprise both known and potential therapeutic compounds. A test compound can be determined to be therapeutic by using the screening methods of the present invention. A "known therapeutic compound" refers to a therapeutic compound that has been shown (e.g., through animal trials or prior experience with administration to humans) to be effective in such treatment or prevention. In preferred embodiments, "test compounds" are agents that modulate apoptosis in cells.

GENERAL DESCRIPTION OF THE INVENTION

As a class of drugs, benzodiazepine compounds have been widely studied and reported to be effective medicaments for treating a number of disease. For example, U.S. Pat. Nos. 4,076,823, 4,110,337, 4,495,101, 4,751,223 and 5,776,946, each incorporated herein by reference in its entirety, report that certain benzodiazepine compounds are effective as analgesic and anti-inflammatory agents. Similarly, U.S. Pat. No. 5,324,726 and U.S. Pat. No. 5,597,915, each incorporated by reference in its entirety, report that certain benzodiazepine compounds are antagonists of cholecystokinin and gastrin and thus might be useful to treat certain gastrointestinal disorders.

Other benzodiazepine compounds have been studied as inhibitors of human neutrophil elastase in the treating of human neutrophil elastase-mediated conditions such as myocardial ischemia, septic shock syndrome, among others (See e.g., U.S. Pat. No. 5,861,380 incorporated herein by reference in its entirety). U.S. Pat. No. 5,041,438, incorporated herein by reference in its entirety, reports that certain benzodiazepine compounds are useful as anti-retroviral agents.

Despite the attention benzodiazepine compounds have drawn, it will become apparent from the description below, that the present invention provides novel compounds (e.g., 1,4-benzodiazepine-2,5-dione compounds) and related compounds and methods of using the novel compounds, as well as known compounds, for treating a variety of diseases.

Benzodiazepine compounds are known to bind to benzodiazepine receptors in the central nervous system (CNS) and thus have been used to treat various CNS disorders including anxiety and epilepsy. Peripheral benzodiazepine receptors have also been identified, which receptors may incidentally also be present in the CNS. The present invention demonstrates that 1,4-benzodiazepine-2,5-dione compounds with, for example, an electron rich heterocycle moiety at the C3 position of the benzodiazepine ring have pro-apoptotic properties consistent with a mechanism that does not result from interaction with the mitochondrial $F_1F_0$-ATPase. The present invention also provides 1,4-benzodiazepine-2,5-dione compounds that demonstrate selective cytotoxicity against T cells as compared to B cells.

DETAILED DESCRIPTION OF THE INVENTION

The present invention provides novel chemical compounds, methods for their discovery, and their therapeutic, research, and diagnostic use. In particular, the present invention provides 1,4-benzodiazepine-2,5-dione compounds, and methods of using 1,4-benzodiazepine-2,5-dione compounds as therapeutic agents to treat a number of conditions associated with the faulty regulation of the processes of programmed cell death, autoimmunity, inflammation, and hyperproliferation, and the like.

Exemplary compositions and methods of the present invention are described in more detail in the following sections: I. Modulators of Cell Death; II. Exemplary Compounds; III. Pharmaceutical compositions, formulations, and exemplary administration routes and dosing considerations; IV. Drug screens; and V. Therapeutic Applications.

The present invention herein incorporates by reference known uses of benzodiazepine compounds, including, but not limited to the uses described in Otto, M. W., et al., (2005) J. Clin. Psychiatry 66 Suppl. 2:34-38; Yoshii, M., et al., (2005) Nippon Yakurigaku Zasshi 125(1):33-36; Yasuda, K. (2004) Nippon Rinsho. 62 Suppl. 12:360-363; Decaudin, D. (2004) 15(8):737-745; Bonnot, O., et al. (2003) Encephale. 29(6): 553-559; Sugiyama, T. (2003) Ryoikibetsu Shokogun Shirizu. 40:489-492; Lacapere, J. J., et al., (2003) Steroids. 68(7-8):569-585; Galiegue, S., et al., (2003) Curr. Med. Chem. 10(16):1563-1572; Papadopoulo, V. (2003) Ann. Pharm. Fr. 61(1):30-50; Goethals, I., et al., (2002) Eur. J. Nucl. Med. Mol. Imaging 30(2):325-328; Castedo, M., et al., (2002) J. Exp. Med. 196(9):1121-1125; Buffett-Jerrott, S. E., et al., (2002) Curr. Pham. Des. 8(1):45-58; Beurdeley-Thomas, A., et al., (2000) J. Nuerooncol. 46(1):45-56; Smyth, W. F., et al., (1998) Electrophoresis 19(16-17):2870-2882; Yoshii, M., et al., (1998) Nihon Shinkei Seishin Yakurigaku Zasshi. 18(2): 49-54; Trimble, M. and Hindmarch, I. (2000) Benzodiazepines, published by Wrighton Biomedical Publishing; and Salamone, S. J. (2001) Benzodiazepines and GHB—Detection and Pharmacology, published by Humana Press.

The practice of the present invention employs, unless otherwise indicated, conventional techniques of organic chemistry, pharmacology, molecular biology (including recombinant techniques), cell biology, biochemistry, and immunology, which are within the skill of the art. Such techniques are explained fully in the literature, such as, "Molecular cloning: a laboratory manual" Second Edition (Sambrook et al., 1989); "Oligonucleotide synthesis" (M. J. Gait, ed., 1984); "Animal cell culture" (R. I. Freshney, ed., 1987); the series "Methods in enzymology" (Academic Press, Inc.); "Handbook of experimental immunology" (D. M. Weir & C. C. Blackwell, eds.); "Gene transfer vectors for mammalian cells" (J. M. Miller & M. P. Calos, eds., 1987); "Current protocols in molecular biology" (F. M. Ausubel et al., eds., 1987, and periodic updates); "PCR: the polymerase chain reaction" (Mullis et al., eds., 1994); and "Current protocols in immunology" (J. E. Coligan et al., eds., 1991), each of which is herein incorporated by reference in its entirety.

I. Modulators of Cell Death

In preferred embodiments, the present invention regulates apoptosis through the exposure of cells to the compounds of the present invention (e.g., 1,4-benzodiazepine-2,5-diones). In particular, the present invention demonstrates that 1,4-benzodiazepine-2,5-diones with, for example, certain heterocycles at the C3 position of the benzodiazepine ring have pro-apoptotic properties consistent with a mechanism that does not result from interaction with the mitochondrial $F_1F_0$-ATPase. The present invention also demonstrates that 1,4-benzodiazepine-2,5-diones with an electron rich heterocycle moiety at the C3 position of the benzodiazepine ring can have pro-apoptotic selectivity for T cells over B cells.

The effect of compounds can be measured by detecting any number of cellular changes. Cell death may be assayed as described herein and in the art. In preferred embodiments, cell lines are maintained under appropriate cell culturing conditions (e.g., gas ($CO_2$), temperature and media) for an appropriate period of time to attain exponential proliferation without density dependent constraints. Cell number and or viability are measured using standard techniques, such as trypan blue exclusion/hemo-cytometry, or MTT dye conversion assay. Alternatively, the cell may be analyzed for the expression of genes or gene products associated with aberrations in apoptosis or necrosis.

II. Exemplary Compounds

Exemplary compounds of the present invention are provided below. Certain 1,4-benzodiazepine-2,5-dione derivatives have been described (see, e.g., U.S. patent application Ser. No. 09/700,101; U.S. Pat. No. 6,506,744; Kamal, et al., 2004 Synlett 14:2533-2535; Hulme, et al., 1998 J. Org. Chem. 63:8021-8022; Raboisson et al., 2005 Bioorg. Med. Chem. Lett. 15:1857-1861; Raboisson et al., 2005 Bioorg. Med. Chem. Lett. 15:765-770; Rabiosson et al., 2005 J. Med. Chem. 48:909-912; each herein incorporated by reference in their entireties). The present invention provides novel 1,4-benzodiazepine-2,5-dione compounds, and uses for 1,4-benzodiazepine-2,5-dione compounds.

Certain embodiments provide a composition comprising a compound described by a formula selected from the group consisting of:

In certain embodiments, the present invention provides a composition comprising novel 1,4-benzodiazepine-2,5-dione compounds. In certain embodiments, the present invention provide a composition comprising a compound described by a formula selected from the group consisting of:

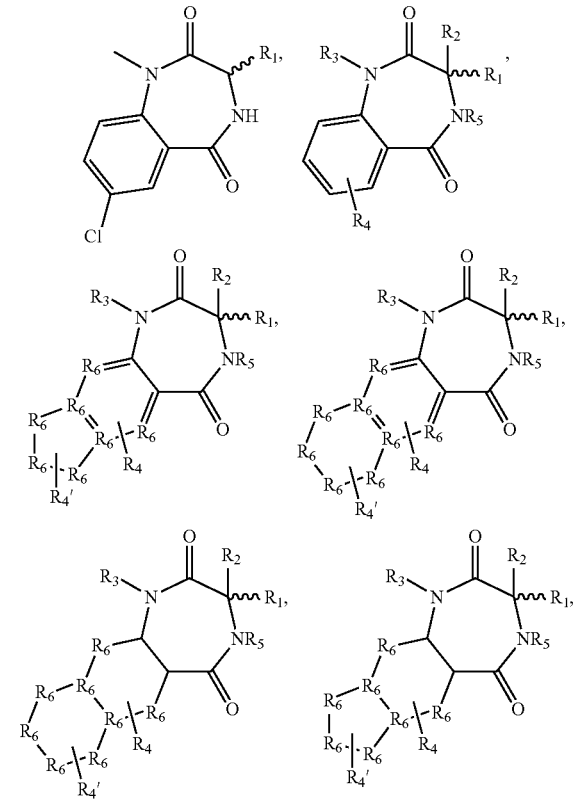

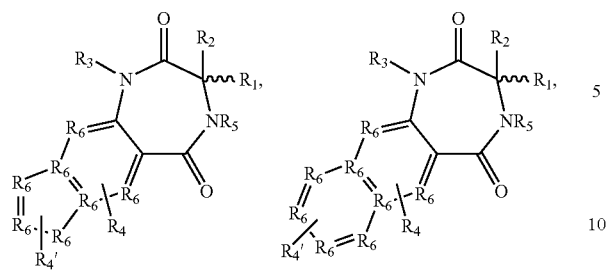
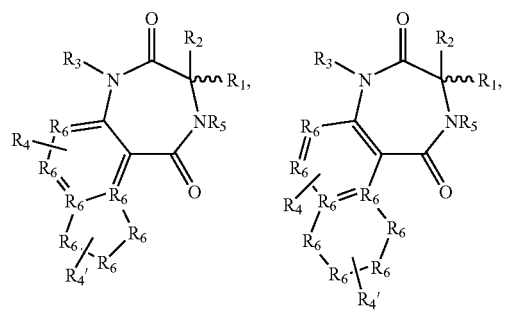
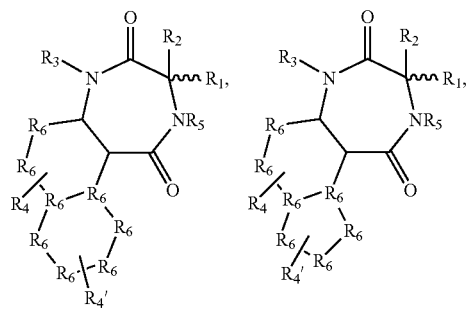
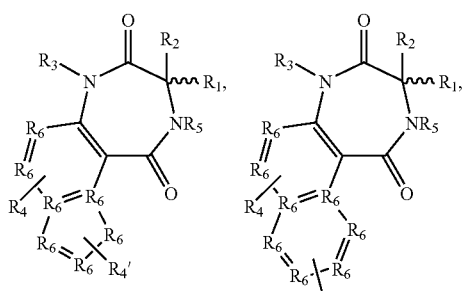
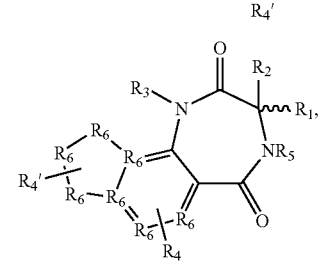
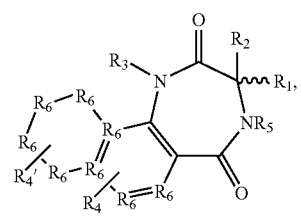
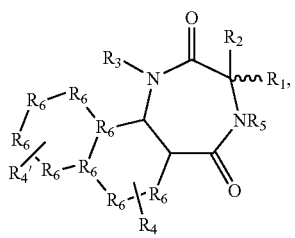
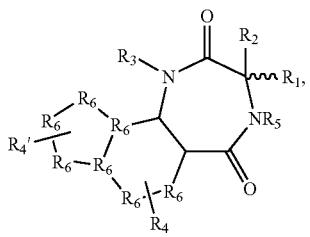
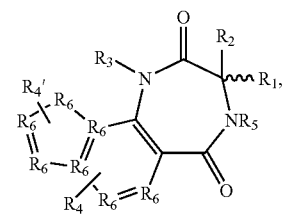
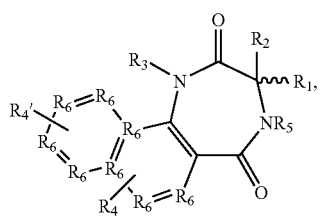
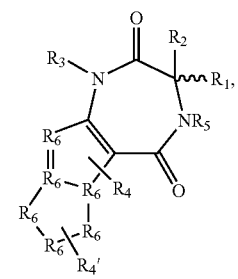
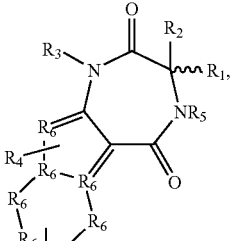
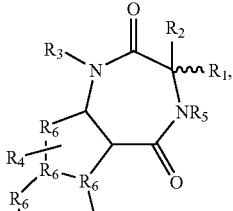
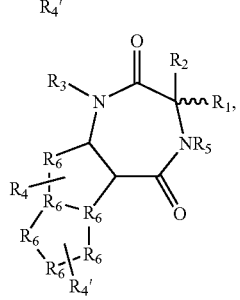

-continued

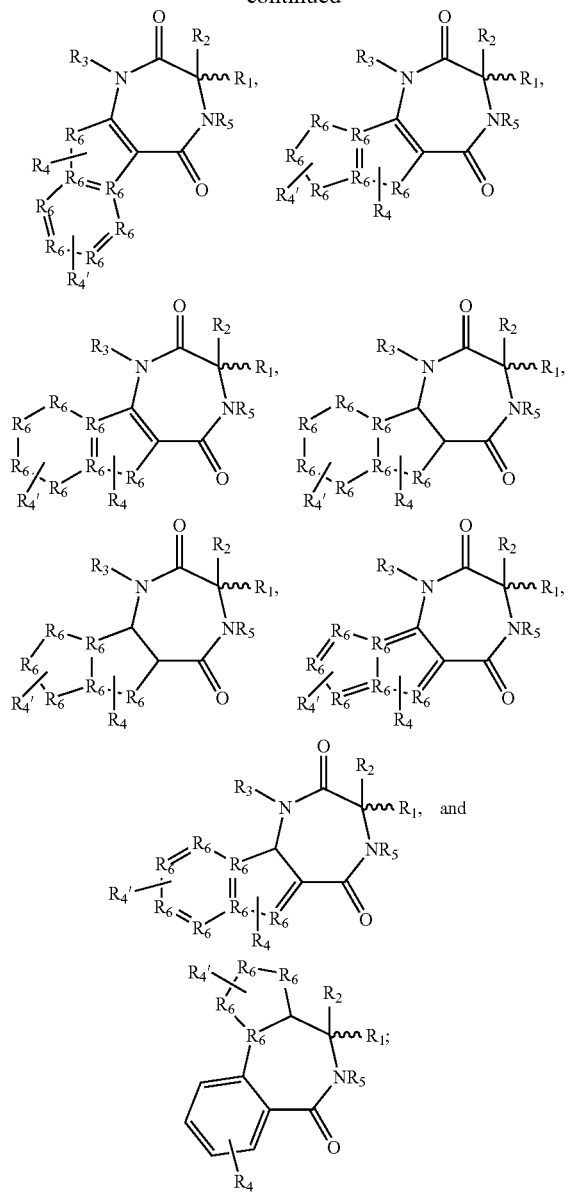

substituted and unsubstituted, including both R and S enantiomeric forms and racemic mixtures.

In some embodiments, R1 is an electron rich heterocycle. In some embodiments, the electron rich heterocycle contains 5 or more heterocyclic atoms.

In some embodiments, $R_1$ is selected from the group consisting of

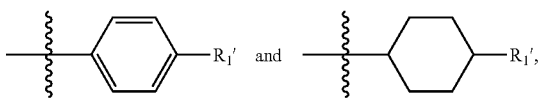

wherein $R_1'$ is selected from the group consisting of cycloalipathic, aryl, substituted aryl, heterocyclic, and substituted heterocyclic.

In some embodiments, $R_2$ is selected from the group consisting of H, alkyl, substituted alky, and $R_1$.

In some embodiments, $R_3$ is selected from the group consisting of H, alkyl, and substituted alkyl.

In some embodiments, R3 is selected from the group consisting of hydrogen; halogen; OH; a chemical moiety comprising an aryl subgroup; a chemical moiety comprising a substituted aryl subgroup; a chemical moiety comprising a cycloaliphatic subgroup; a chemical moiety comprising a substituted cycloaliphatic subgroup; a chemical moiety comprising a heterocyclic subgroup; a chemical moiety comprising a substituted heterocyclic subgroup; a chemical moiety comprising at least one ester subgroup; a chemical moiety comprising at least one ether subgroup; a linear or branched, saturated or unsaturated, substituted, aliphatic chain having at least 2 carbons; a chemical moiety comprising Sulfur; a chemical moiety comprising Nitrogen; —OR—, wherein R is selected from the group consisting of a chemical moiety comprising an aryl subgroup; a chemical moiety comprising a substituted aryl subgroup; a chemical moiety comprising a cycloaliphatic subgroup; a chemical moiety comprising a substituted cycloaliphatic subgroup; a chemical moiety comprising a heterocyclic subgroup; a chemical moiety comprising a substituted heterocyclic subgroup; a linear or branched, saturated or unsaturated, substituted or non-substituted, aliphatic chain having at least 2 carbons; a chemical moiety comprising at least one ester subgroup; a chemical moiety comprising at least one ether subgroup; a chemical moiety comprising Sulfur; a chemical moiety comprising Nitrogen.

In some embodiments, R3 is selected from group consisting of: napthalene; phenol; 1-Napthalenol; 2-Napthalenol;

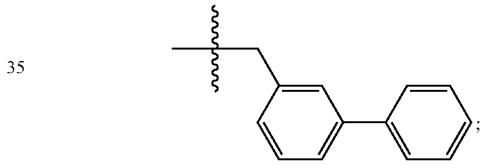

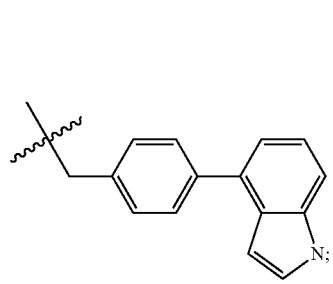

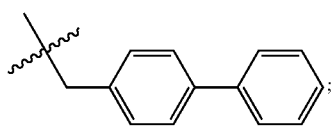

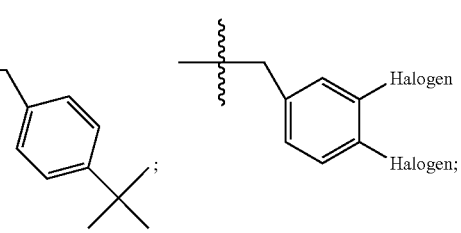

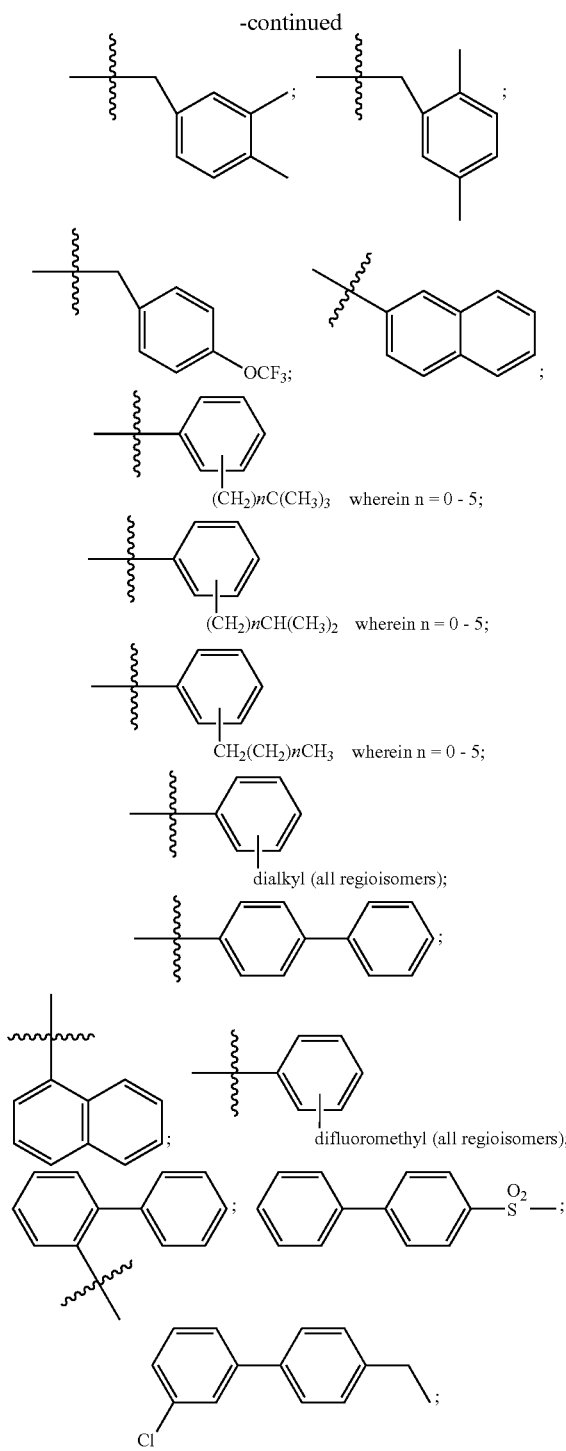

quinolines, and all aromatic regioisomers.

In some embodiments, the R1 and R3 groups may be interchanged (e.g., in some embodiments, the R1 group is positioned at the first position of the benzodiazepine ring and the R3 group is positioned at the third position of the benzodiazepine ring; in some embodiments, the R1 group is positioned at the third position of the benzodiazepine ring and the R3 group is positioned at the first position of the benzodiazepine ring).

In embodiments, $R_4$ and $R_4'$ is independently selected from the group consisting of $CH_3$, halogen, $SO_2R_4''$, $SO_2N(R_4'')_2$, $OR_4''$, $N(R_4'')_2$, $CON(R_4'')_2$, $NHCOR_4''$, $NHSO_2R4'$, alkyl, mono-substituted alkyl, di-substituted alkyl, tri-substituted alkyl; wherein $R_4''$ is selected from the group consisting of halogen, H, alkyl, mono-substituted alkyl, di-substituted alkyl, tri-substituted alkyl, aryl, mono-substituted aryl, di-substituted aryl, tri-substituted aryl, cycloalipathic, mono-substituted cycloalipathic, di-substituted cycloalipathic, tri-substituted cycloalipathic.

In some embodiments, $R_5$ is selected from the group consisting of H, alkyl, mono-substituted aryl, di-substituted aryl, and tri-substituted aryl.

In some embodiments, R6 is selected from the group consisting of C, N or S.

In some embodiments, R1 is selected from the group consisting of:

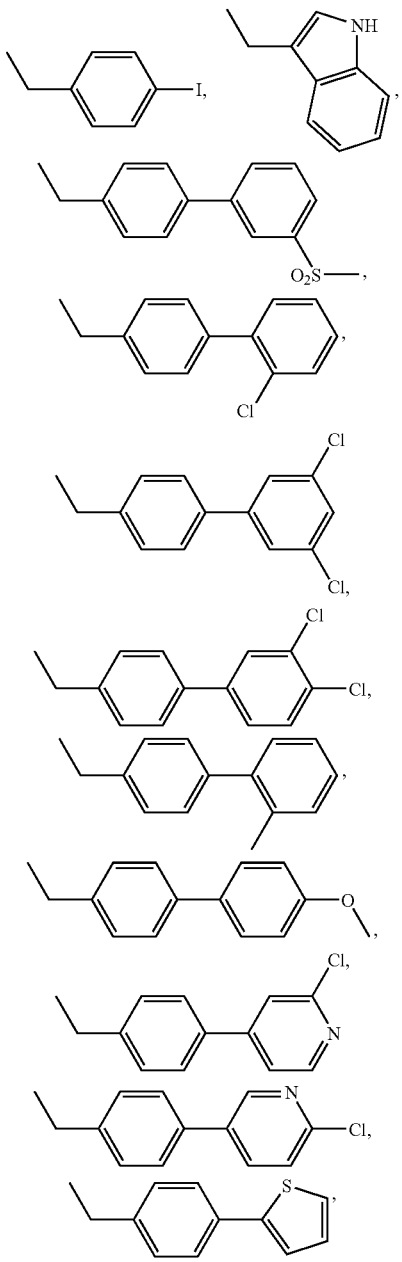

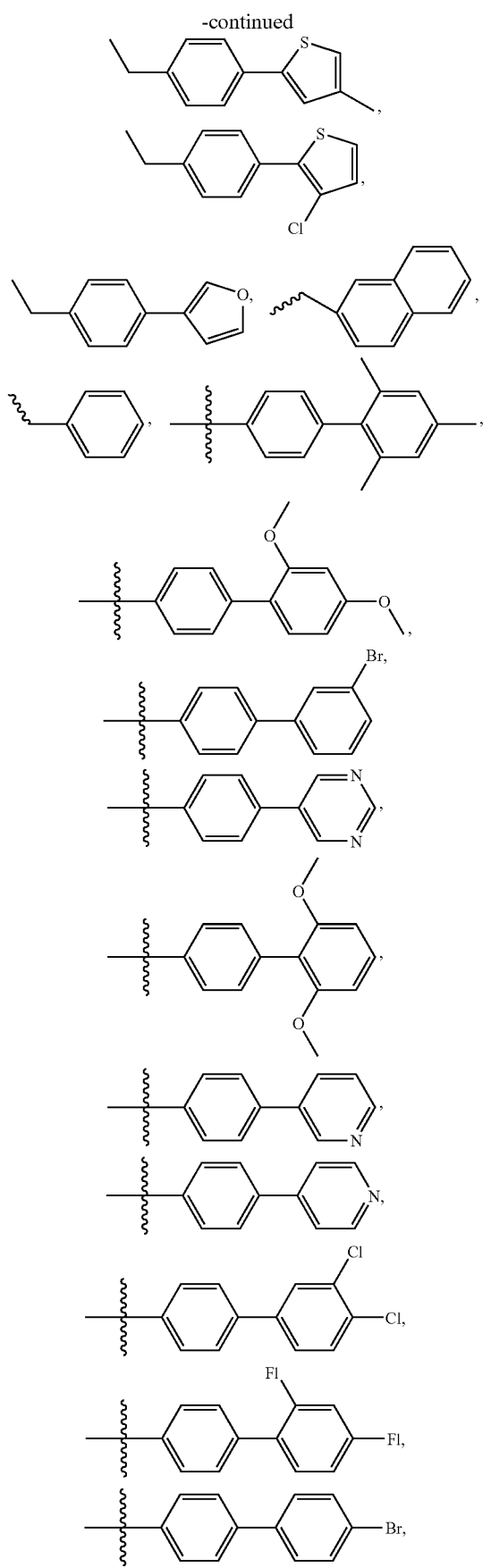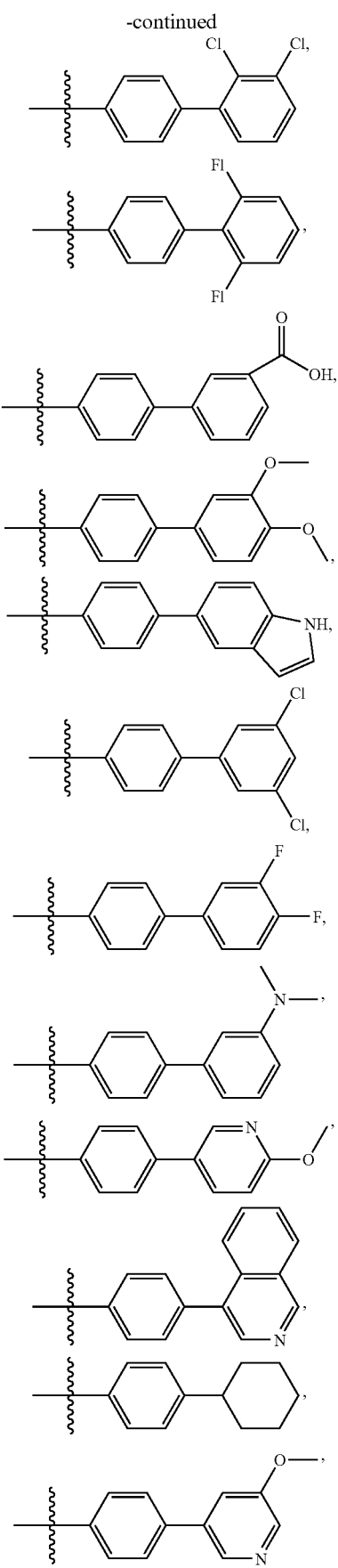

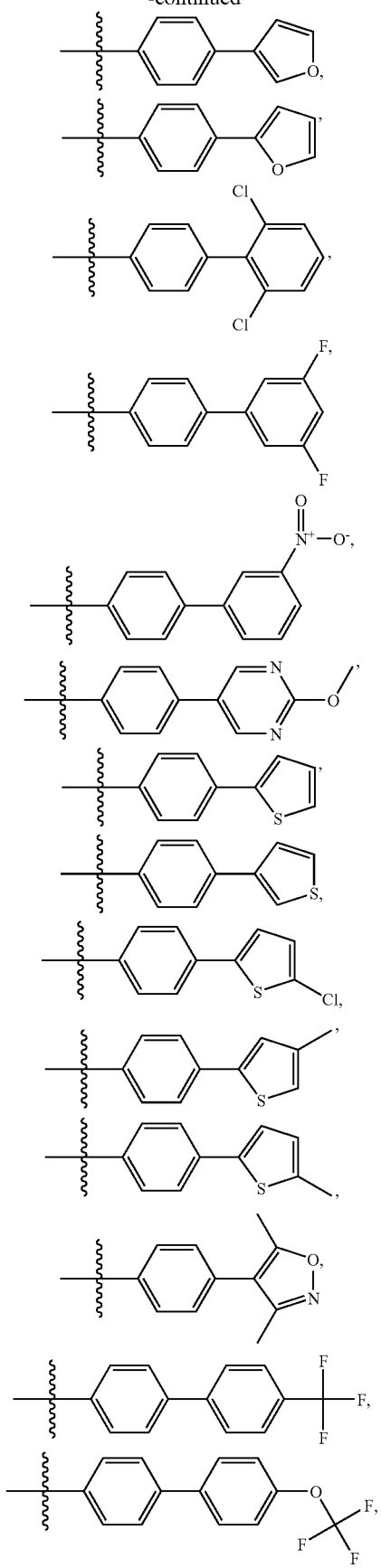
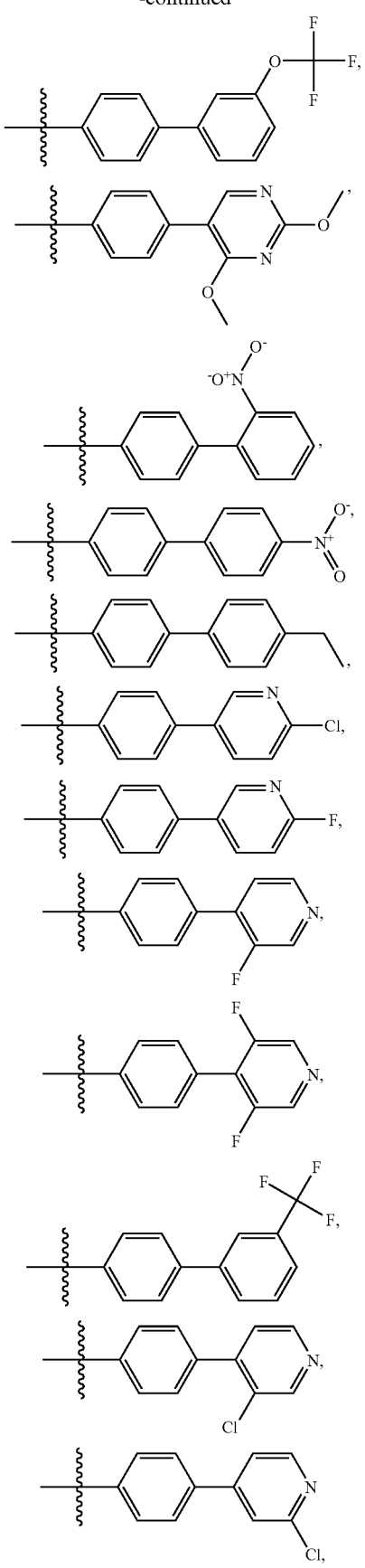

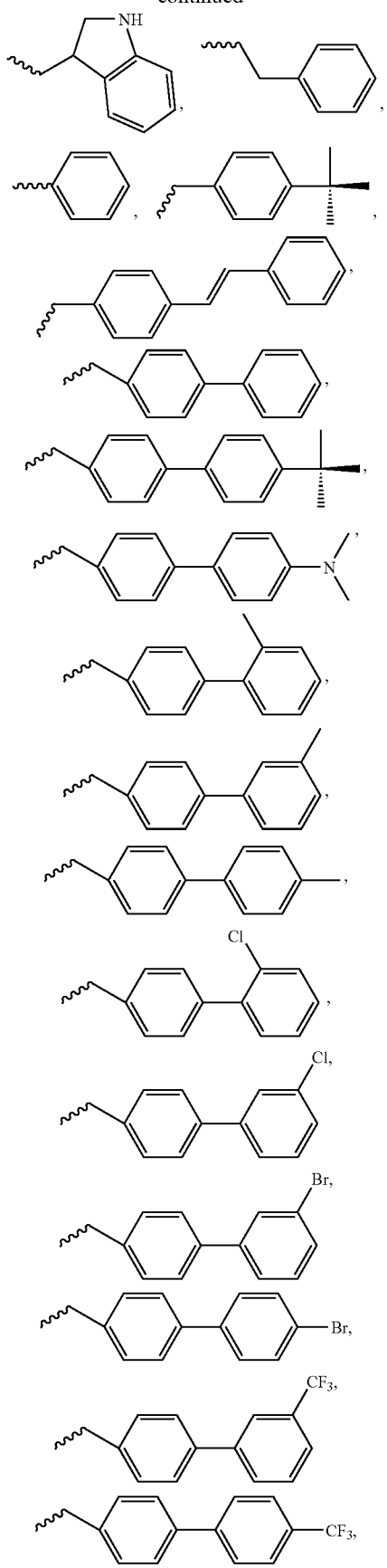
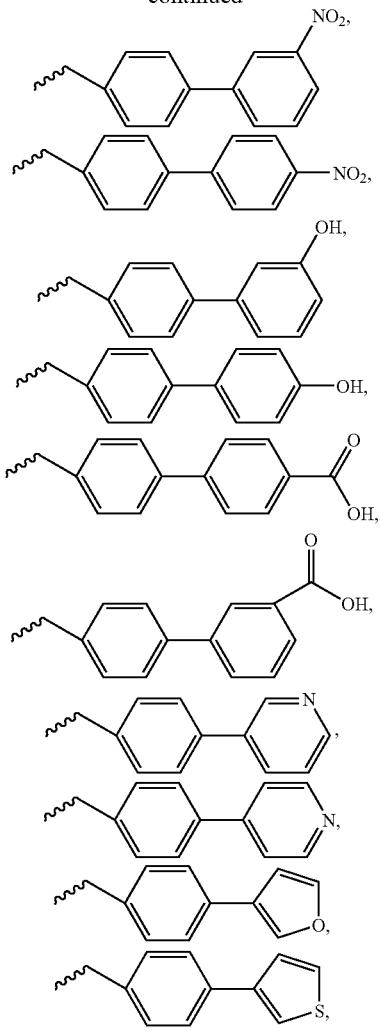
substituted and unsubstituted, and derivatives thereof.
Certain 1,4-benzodiazepine-2,5-dione compounds of the present invention include, but are not limited to,
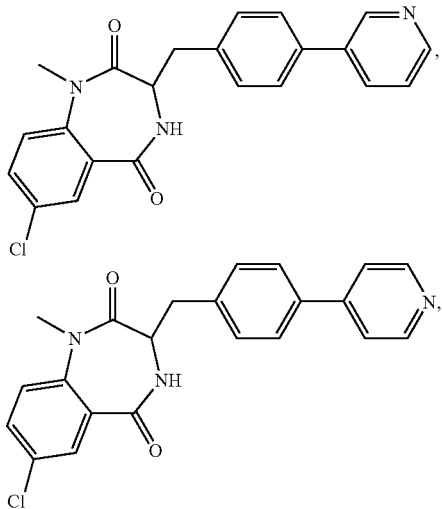

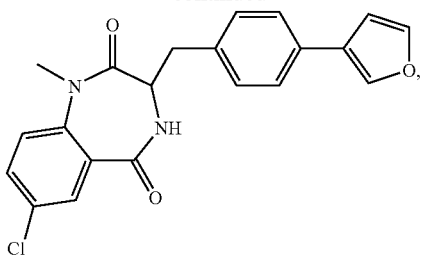

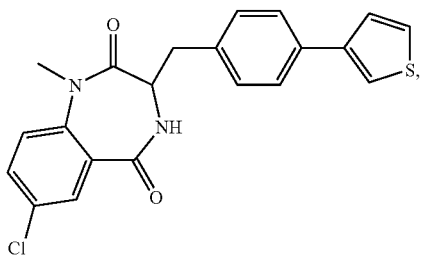

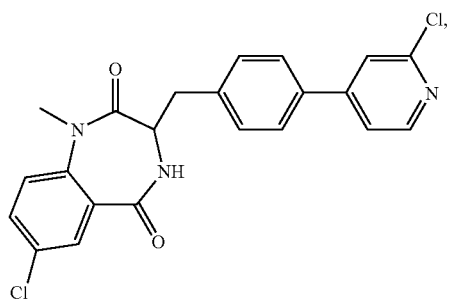

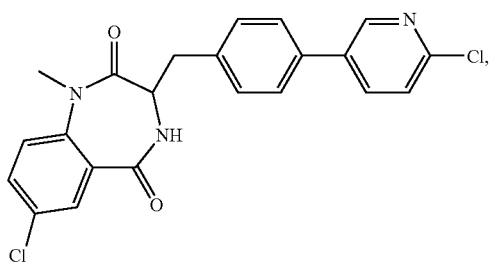

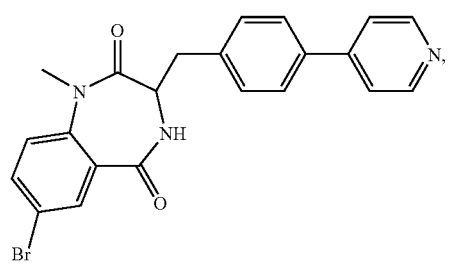

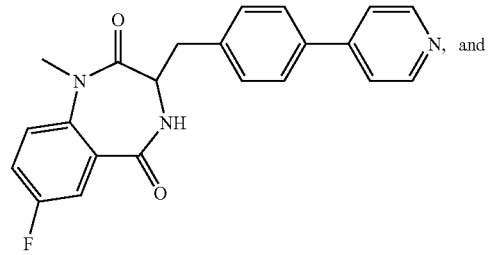

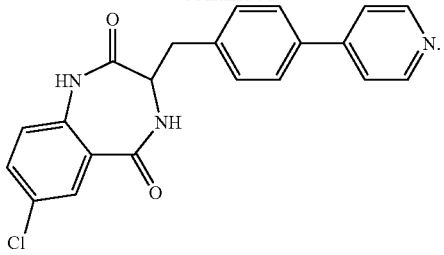

From the above description, it is apparent that many specific examples are represented by the generic formulas presented above. A wide variety of sub combinations arising from selecting a particular group at each substituent position are possible and all such combinations are within the scope of this invention. The experimental examples, provided below, describe biological activities of these compounds and provide assays for assessing activities of derivatives or other related compounds.

In summary, a large number of compounds are presented herein. Any one or more of these compounds can be used to treat a variety of dysregulatory disorders related to cellular death as described elsewhere herein. Additionally, any one or more of these compounds can be used in combination with at least one other therapeutic agent (e.g., potassium channel openers, calcium channel blockers, sodium hydrogen exchanger inhibitors, antiarrhythmic agents, antiatherosclerotic agents, anticoagulants, antithrombotic agents, prothrombolytic agents, fibrinogen antagonists, diuretics, antihypertensive agents, ATPase inhibitors, mineralocorticoid receptor antagonists, phosphodiesterase inhibitors, antidiabetic agents, anti-inflammatory agents, antioxidants, angiogenesis modulators, antiosteoporosis agents, hormone replacement therapies, hormone receptor modulators, oral contraceptives, antiobesity agents, antidepressants, antianxiety agents, antipsychotic agents, antiproliferative agents, antitumor agents, antiulcer and gastroesophageal reflux disease agents, growth hormone agents and/or growth hormone secretagogues, thyroid mimetics, anti-infective agents, antiviral agents, antibacterial agents, antifungal agents, cholesterol/lipid lowering agents and lipid profile therapies, and agents that mimic ischemic preconditioning and/or myocardial stunning, antiatherosclerotic agents, anticoagulants, antithrombotic agents, antihypertensive agents, antidiabetic agents, and antihypertensive agents selected from ACE inhibitors, AT-1 receptor antagonists, ET receptor antagonists, dual ET/AII receptor antagonists, and vasopepsidase inhibitors, or an antiplatelet agent selected from GPIIb/IIIa blockers, $P2Y_1$, and $P2Y_{12}$ antagonists, thromboxane receptor antagonists, and aspirin) cellular activating agents in along with a pharmaceutically-acceptable carrier or diluent in a pharmaceutical composition. The above-described compounds can also be used in drug screening assays and other diagnostic and research methods.

III. Pharmaceutical Compositions, Formulations, and Exemplary Administration Routes and Dosing Considerations Exemplary embodiments of various contemplated medicaments and pharmaceutical compositions are provided below.

A. Preparing Medicaments

The compounds of the present invention are useful in the preparation of medicaments to treat a variety of conditions associated with dysregulation of cell death, aberrant cell growth and hyperproliferation.

In addition, the compounds are also useful for preparing medicaments for treating other disorders wherein the effectiveness of the compounds are known or predicted. Such disorders include, but are not limited to, autoimmune disorders disorders. The methods and techniques for preparing medicaments of a compound of the present invention are well-known in the art. Exemplary pharmaceutical formulations and routes of delivery are described below.

One of skill in the art will appreciate that any one or more of the compounds described herein, including the many specific embodiments, are prepared by applying standard pharmaceutical manufacturing procedures. Such medicaments can be delivered to the subject by using delivery methods that are well-known in the pharmaceutical arts.

B. Exemplary Pharmaceutical Compositions and Formulation

In some embodiments of the present invention, the compositions are administered alone, while in some other embodiments, the compositions are preferably present in a pharmaceutical formulation comprising at least one active ingredient/agent, as defined above, together with a solid support or alternatively, together with one or more pharmaceutically acceptable carriers and optionally other therapeutic agents (e.g., a benzodiazepine compound as described in 60/812,270, 60/802,394, 60/607,599, and 60/641,040, and U.S. patent application Ser. Nos. 11/445,010, 11/324,419, 11/176,719, 11/110,228, 10/935,333, 10/886,450, 10/795,535, 10/634,114, 10/427,211, 10/427,212, 10/217,878, 09/767,283, 09/700,101, and related applications; each herein incorporated by reference in their entireties). Each carrier should be "acceptable" in the sense that it is compatible with the other ingredients of the formulation and not injurious to the subject.

Contemplated formulations include those suitable oral, rectal, nasal, topical (including transdermal, buccal and sublingual), vaginal, parenteral (including subcutaneous, intramuscular, intravenous and intradermal) and pulmonary administration. In some embodiments, formulations are conveniently presented in unit dosage form and are prepared by any method known in the art of pharmacy. Such methods include the step of bringing into association the active ingredient with the carrier which constitutes one or more accessory ingredients. In general, the formulations are prepared by uniformly and intimately bringing into association (e.g., mixing) the active ingredient with liquid carriers or finely divided solid carriers or both, and then if necessary shaping the product.

Formulations of the present invention suitable for oral administration may be presented as discrete units such as capsules, cachets or tablets, wherein each preferably contains a predetermined amount of the active ingredient; as a powder or granules; as a solution or suspension in an aqueous or non-aqueous liquid; or as an oil-in-water liquid emulsion or a water-in-oil liquid emulsion. In other embodiments, the active ingredient is presented as a bolus, electuary, or paste, etc.

In some embodiments, tablets comprise at least one active ingredient and optionally one or more accessory agents/carriers are made by compressing or molding the respective agents. In preferred embodiments, compressed tablets are prepared by compressing in a suitable machine the active ingredient in a free-flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface-active or dispersing agent. Molded tablets are made by molding in a suitable machine a mixture of the powdered compound (e.g., active ingredient) moistened with an inert liquid diluent. Tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Pharmaceutical compositions for topical administration according to the present invention are optionally formulated as ointments, creams, suspensions, lotions, powders, solutions, pastes, gels, sprays, aerosols or oils. In alternative embodiments, topical formulations comprise patches or dressings such as a bandage or adhesive plasters impregnated with active ingredient(s), and optionally one or more excipients or diluents. In preferred embodiments, the topical formulations include a compound(s) that enhances absorption or penetration of the active agent(s) through the skin or other affected areas. Examples of such dermal penetration enhancers include dimethylsulfoxide (DMSO) and related analogues.

If desired, the aqueous phase of a cream base includes, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof.

In some embodiments, oily phase emulsions of this invention are constituted from known ingredients in a known manner. This phase typically comprises a lone emulsifier (otherwise known as an emulgent), it is also desirable in some embodiments for this phase to further comprises a mixture of at least one emulsifier with a fat or an oil or with both a fat and an oil.

Preferably, a hydrophilic emulsifier is included together with a lipophilic emulsifier so as to act as a stabilizer. In some embodiments it is also preferable to include both an oil and a fat. Together, the emulsifier(s) with or without stabilizer(s) make up the so-called emulsifying wax, and the wax together with the oil and/or fat make up the so-called emulsifying ointment base which forms the oily dispersed phase of the cream formulations.

Emulgents and emulsion stabilizers suitable for use in the formulation of the present invention include Tween 60, Span 80, cetostearyl alcohol, myristyl alcohol, glyceryl monostearate and sodium lauryl sulfate.

The choice of suitable oils or fats for the formulation is based on achieving the desired properties (e.g., cosmetic properties), since the solubility of the active compound/agent in most oils likely to be used in pharmaceutical emulsion formulations is very low. Thus creams should preferably be a non-greasy, non-staining and washable products with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent for the agent.

Formulations for rectal administration may be presented as a suppository with suitable base comprising, for example, cocoa butter or a salicylate.

Formulations suitable for vaginal administration may be presented as pessaries, creams, gels, pastes, foams or spray formulations containing in addition to the agent, such carriers as are known in the art to be appropriate.

Formulations suitable for nasal administration, wherein the carrier is a solid, include coarse powders having a particle size, for example, in the range of about 20 to about 500 microns which are administered in the manner in which snuff is taken, i.e., by rapid inhalation (e.g., forced) through the nasal passage from a container of the powder held close up to the nose. Other suitable formulations wherein the carrier is a liquid for administration include, but are not limited to, nasal sprays, drops, or aerosols by nebulizer, an include aqueous or oily solutions of the agents.

Formulations suitable for parenteral administration include aqueous and non-aqueous isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. In some embodiments, the formulations are presented/formulated in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily subdose, as herein above-recited, or an appropriate fraction thereof, of an agent.

It should be understood that in addition to the ingredients particularly mentioned above, the formulations of this invention may include other agents conventional in the art having regard to the type of formulation in question, for example, those suitable for oral administration may include such further agents as sweeteners, thickeners and flavoring agents. It also is intended that the agents, compositions and methods of this invention be combined with other suitable compositions and therapies. Still other formulations optionally include food additives (suitable sweeteners, flavorings, colorings, etc.), phytonutrients (e.g., flax seed oil), minerals (e.g., Ca, Fe, K, etc.), vitamins, and other acceptable compositions (e.g., conjugated linoelic acid), extenders, and stabilizers, etc.

C. Exemplary Administration Routes and Dosing Considerations

Various delivery systems are known and can be used to administer therapeutic agents (e.g., exemplary compounds as described in Section II above) of the present invention, e.g., encapsulation in liposomes, microparticles, microcapsules, receptor-mediated endocytosis, and the like. Methods of delivery include, but are not limited to, intra-arterial, intramuscular, intravenous, intranasal, and oral routes. In specific embodiments, it may be desirable to administer the pharmaceutical compositions of the invention locally to the area in need of treatment; this may be achieved by, for example, and not by way of limitation, local infusion during surgery, injection, or by means of a catheter.

The agents identified can be administered to subjects or individuals susceptible to or at risk of developing pathological growth of target cells and correlated conditions. When the agent is administered to a subject such as a mouse, a rat or a human patient, the agent can be added to a pharmaceutically acceptable carrier and systemically or topically administered to the subject. To identify patients that can be beneficially treated, a tissue sample is removed from the patient and the cells are assayed for sensitivity to the agent. Therapeutic amounts are empirically determined and vary with the pathology being treated, the subject being treated and the efficacy and toxicity of the agent.

In some embodiments, in vivo administration is effected in one dose, continuously or intermittently throughout the course of treatment. Methods of determining the most effective means and dosage of administration are well known to those of skill in the art and vary with the composition used for therapy, the purpose of the therapy, the target cell being treated, and the subject being treated. Single or multiple administrations are carried out with the dose level and pattern being selected by the treating physician.

Suitable dosage formulations and methods of administering the agents are readily determined by those of skill in the art. Preferably, the compounds are administered at about 0.01 mg/kg to about 200 mg/kg, more preferably at about 0.1 mg/kg to about 100 mg/kg, even more preferably at about 0.5 mg/kg to about 50 mg/kg. When the compounds described herein are co-administered with another agent (e.g., as sensitizing agents), the effective amount may be less than when the agent is used alone.

The pharmaceutical compositions can be administered orally, intranasally, parenterally or by inhalation therapy, and may take the form of tablets, lozenges, granules, capsules, pills, ampoules, suppositories or aerosol form. They may also take the form of suspensions, solutions and emulsions of the active ingredient in aqueous or nonaqueous diluents, syrups, granulates or powders. In addition to an agent of the present invention, the pharmaceutical compositions can also contain other pharmaceutically active compounds or a plurality of compounds of the invention.

More particularly, an agent of the present invention also referred to herein as the active ingredient, may be administered for therapy by any suitable route including, but not limited to, oral, rectal, nasal, topical (including, but not limited to, transdermal, aerosol, buccal and sublingual), vaginal, parental (including, but not limited to, subcutaneous, intramuscular, intravenous and intradermal) and pulmonary. It is also appreciated that the preferred route varies with the condition and age of the recipient, and the disease being treated.

Ideally, the agent should be administered to achieve peak concentrations of the active compound at sites of disease. This may be achieved, for example, by the intravenous injection of the agent, optionally in saline, or orally administered, for example, as a tablet, capsule or syrup containing the active ingredient.

Desirable blood levels of the agent may be maintained by a continuous infusion to provide a therapeutic amount of the active ingredient within disease tissue. The use of operative combinations is contemplated to provide therapeutic combinations requiring a lower total dosage of each component antiviral agent than may be required when each individual therapeutic compound or drug is used alone, thereby reducing adverse effects.

D. Exemplary Co-Administration Routes and Dosing Considerations

The present invention also includes methods involving co-administration of the compounds described herein with one or more additional active agents. Indeed, it is a further aspect of this invention to provide methods for enhancing prior art therapies and/or pharmaceutical compositions by co-administering a compound of this invention. In co-administration procedures, the agents may be administered concurrently or sequentially. In one embodiment, the compounds described herein are administered prior to the other active agent(s). The pharmaceutical formulations and modes of administration may be any of those described above. In addition, the two or more co-administered chemical agents, biological agents or radiation may each be administered using different modes or different formulations.

The agent or agents to be co-administered depends on the type of condition being treated. For example, when the condition being treated is cancer, the additional agent can be a chemotherapeutic agent or radiation. When the condition being treated is an autoimmune disorder, the additional agent can be an immunosuppressant or an anti-inflammatory agent. When the condition being treated is chronic inflammation, the additional agent can be an anti-inflammatory agent. The additional agents to be co-administered, such as anticancer, immunosuppressant, anti-inflammatory, and can be any of the well-known agents in the art, including, but not limited to, those that are currently in clinical use. The determination of appropriate type and dosage of radiation treatment is also within the skill in the art or can be determined with relative ease.

Treatment of the various conditions associated with abnormal apoptosis is generally limited by the following two major factors: (1) the development of drug resistance and (2) the toxicity of known therapeutic agents. In certain cancers, for example, resistance to chemicals and radiation therapy has been shown to be associated with inhibition of apoptosis. Some therapeutic agents have deleterious side effects, including non-specific lymphotoxicity, renal and bone marrow toxicity.

The methods described herein address both these problems. Drug resistance, where increasing dosages are required to achieve therapeutic benefit, is overcome by co-administering the compounds described herein with the known agent. The compounds described herein sensitize target cells to known agents (and vice versa) and, accordingly, less of these agents are needed to achieve a therapeutic benefit.

The sensitizing function of the claimed compounds also addresses the problems associated with toxic effects of known therapeutics. In instances where the known agent is toxic, it is desirable to limit the dosages administered in all cases, and particularly in those cases were drug resistance has increased the requisite dosage. When the claimed compounds are co-administered with the known agent, they reduce the dosage required which, in turn, reduces the deleterious effects. Further, because the claimed compounds are themselves both effective and non-toxic in large doses, co-administration of proportionally more of these compounds than known toxic therapeutics will achieve the desired effects while minimizing toxic effects.

IV. Drug Screens

In some embodiments of the present invention, the compounds of the present invention, and other potentially useful compounds, are screened for pro-apoptotic properties consistent with a mechanism that does not entail interaction with the mitochondrial $F_1F_0$-ATPase. In preferred embodiments of the present invention, the compounds of the present invention, and other potentially useful compounds, are screened for pro-apoptotic selectivity for T cells over B cells.

A number of suitable screens for measuring the binding affinity of drugs and other small molecules to receptors are known in the art. In some embodiments, binding affinity screens are conducted in in vitro systems. In other embodiments, these screens are conducted in in vivo or ex vivo systems.

V. Therapeutic Application

In particularly preferred embodiments, the compositions of the present invention are contemplated to provide therapeutic benefits to patients suffering from any one or more of a number of conditions (e.g., diseases characterized by dysregulation of necrosis and/or apoptosis processes in a cell or tissue, disease characterized by aberrant cell growth and/or hyperproliferation, autoimmune diseases, haematologic malignancies resulting from aberrant survival and expansion of B and T cells in central and peripheral lymphoid organs, etc.) by modulating (e.g., inhibiting or promoting) apoptosis in affected cells or tissues. In further preferred embodiments, the compositions of the present invention are used to treat autoimmune/chronic inflammatory conditions.

In particularly preferred embodiments, the compositions of the present invention regulate apoptosis through the exposure of cells to the compounds of the present invention (e.g., 1,4-benzodiazepine-2,5-diones). In particular, the present invention demonstrates that 1,4-benzodiazepine-2,5-diones with, for example, an electron rich heterocycle moiety at the C3 position of the benzodiazepine ring have pro-apoptotic properties consistent with a mechanism that does not result from interaction with the mitochondrial $F_1F_0$-ATPase. The present invention also demonstrates that 1,4-benzodiazepine-2,5-diones with an electron rich heterocycle moiety at the C3 position of the benzodiazepine ring have pro-apoptotic selectivity for T cells over B cells.

Accordingly, preferred methods embodied in the present invention provide therapeutic benefits to patients by providing compounds of the present invention that modulate (e.g., inhibiting or promoting) cellular apoptosis in affected cells or tissues without interacting with the mitochondrial $F_1F_0$-ATPase.

In some embodiments, compounds potentially useful in methods of the present invention are screened against the National Cancer Institute's (NCI-60) cancer cell lines for efficacy. (See e.g., A. Monks et al., J. Natl. Cancer Inst., 83:757-766 [1991]; and K. D. Paull et al., J. Natl. Cancer Inst., 81:1088-1092 [1989]). Additional screens suitable screens (e.g., autoimmunity disease models, etc.) are within the skill in the art.

In one aspect, derivatives (e.g., pharmaceutically acceptable salts, analogs, stereoisomers, and the like) of the exemplary compounds or other suitable compounds are also contemplated as being useful in the methods of the present invention.

Those skilled in the art of preparing pharmaceutical compounds and formulations will appreciate that when selecting optional compounds for use in the methods disclosed herein, that suitability considerations include, but are not limited to, the toxicity, safety, efficacy, availability, and cost of the particular compounds.

EXAMPLES

The following examples are provided to demonstrate and further illustrate certain preferred embodiments of the present invention and are not to be construed as limiting the scope thereof.

Example 1

This example describes the formulation of exemplary 1,4-benzodiazepine-2,5-diones. As shown in FIG. 1, Bz-423 is a pro-apoptotic 1,4 benzodiazepine with potent activity in animal models of lupus (see, e.g., Blatt, N. B., et al., J. Clin. Invest. 2002, 10, 1123; Bednarski, J. J., et al., Arthritis Rheum. 2003, 48, 757; each herein incorporated by reference in their entireties). Bz-423 binds to the oligomycin sensitivity conferring protein (OSCP) component of the mitochondrial $F_1F_0$-ATPase (see, e.g., Johnson, K. M., et al., Chemistry and Biology. 2005, 12, 485; herein incorporated by reference in its entirety). Bz-423 inhibits the enzyme, which produces a state 3 to state 4 transition within the mitochondrial respiratory chain (MRC), ultimately resulting in the production of $O_2^-$ from MRC complex III. This reactive oxygen species functions as a signal—initiating a tightly-regulated apoptotic process (see, e.g., Johnson, K. M., et al., Chemistry and Biology. 2005, 12, 485; herein incorporated by reference in its entirety).

Figure 2:
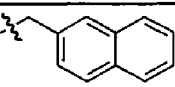
FIG. 2 shows exemplary compounds of the present invention and their biological activities.
Figure 2:
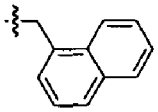
Figure 2:
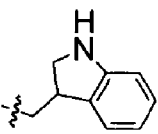
Figure 2:
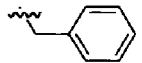
Figure 2:
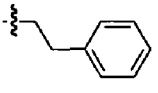
Figure 2:
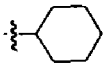
Figure 2:
Figure 2:
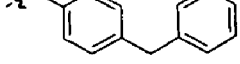
Figure 2:
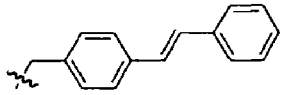
Figure 2:
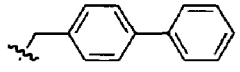
Figure 2:
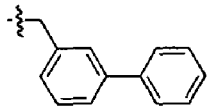

Previous studies revealed that a hydrophobic aromatic substituent at C3 along with the phenolic hydroxyl group is required for the cytotoxic activity of Bz-423. As part of efforts to further define the elements of Bz-423 required for inhibiting the $F_1F_0$-ATPase, a series of 1,4-benzodiazepine-2,5-diones were synthesized as intermediates for other chemistry. Most of these compounds were cytotoxic and unlike Bz-423, many were more selective for T cells compared to B cells (FIG. 2). Replacing the napthyl moiety with other hydrophobic groups of comparable size (2, 3), but which occupy different space, had relatively small effects on activity compared with 1, and in some cases altered the selectivity. By contrast, reducing the size of the C3 group (4, 5) was not tolerated. Given the similarity between the structures in FIG. 2 and the pro-apoptotic 1,4-benzodiazepines previously reported (see, e.g., Johnson, K. M., et al., Chemistry and Biology. 2005, 12, 485; herein incorporated by reference in its entirety), experiments were conducted to determine if the 1,4-benzodiazepine-2,5-dione compounds inhibit the $F_1F_0$-ATPase and generate $O_2^-$ in the same manner as Bz-423. Compounds listed in FIG. 2 neither blocked the $F_1F_0$-ATPase nor inhibited by agents that specifically scavenge superoxide. These results indicated that the 1,4-benzodiazepine-2,5-dione compounds shown in FIG. 2 have a different molecular target and apoptotic mechanism than Bz-423. By contrast, the m-biphenyl analog inhibited ATP hydrolysis while not blocking synthesis, similar to previously reported 1,4-benzodiazepine (see, e.g., Hamann, L. G., et al., Bio. Med. Chem. Lett. 2004, 14, 1031; herein incorporated by reference in its entirety).

Example 2

Figure 3:
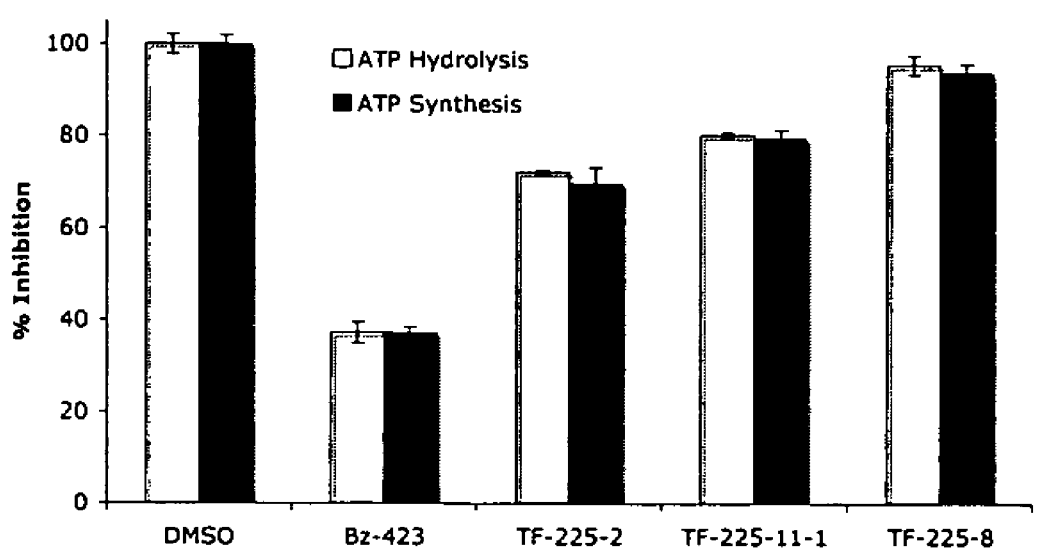
FIG. 3 shows ATP Synthesis and Hydrolysis Inhibition Graph for 1,4-benzodiazepine-2,5-diones.

This example describes the optimization of the novel 1,4-benzodiazepine-2,5-dione compounds of the present invention. The data in FIG. 2 show that the size of the C3 is important for the activity of the 1,4-benzodiazepine-2,5-dione compounds. Moreover, these data suggest that it is possible to optimize potency and selectivity based on the biphenyl or 2-napthylene C3 side chains. A range of substituted biphenyls can be prepared readily by Suzuki couplings of aryl halides with commercially available boronic acids (see, e.g., Suzuki, A. Acc. Chem. Res. 1982, 15, 178; herein incorporated by reference in its entirety). Therefore, the relationship between the stereoelectronics of the C3 side chain and cytotoxicity of the 1,4-benzodiazepine-2,5-dione compounds, was further evaluated by synthesizing substituted analogs of 10 (FIG. 3).

Figure 4:
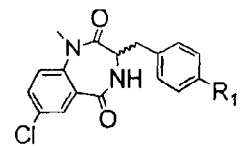
FIG. 4 shows exemplary compounds of the present invention and their biological activities.
Figure 4:
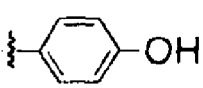
Figure 4:
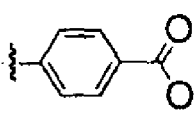
Figure 4:
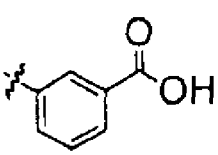
Figure 4:
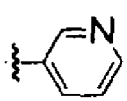
Figure 4:
Figure 4:
Figure 4:
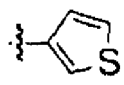

In the first group of derivatives a methyl group or chlorine atom was substituted at each of the 2', 3', or 4'-positions. Analysis of these compounds revealed that substitution had little effect of killing T cells but improved the potency against B cells. Since substitution at either the 3' or 4' position led to the greatest improvement in potency, substitutions at those positions was further explored. The addition of electron rich substituents to the meta and para positions (26, 27) increased potency, whereas the carboxylic acid 28 had the reverse effect. In addition, electron rich, heterocyclic aromatic rings (30-33) provided selectively potent compounds, namely (30, 31). Collectively, this data indicate that electron rich aromatic heterocycles at $R_1$ of FIG. 4 provide optimal activity and selectivity, although the present invention is not limited to such compounds.

Figure 5:
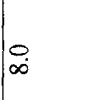
FIG. 5 presents additional selectivity data for additional 1,4-benzodiazepine-2,5-dione compounds of the present invention.
Figure 5:
Figure 5:
Figure 5:
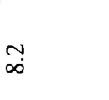
Figure 5:
Figure 5:
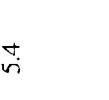
Figure 5:
Figure 5:
Figure 5:
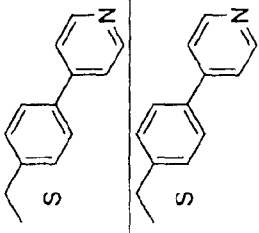
Figure 5:
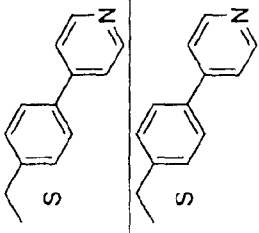

FIG. 5 presents additional selectivity data for additional 1,4-benzodiazepine-2,5-dione compounds of the present invention. Ramos EC50 refers to the concentration of drug required to 50% of Ramos B cells and Jurkat EC50 refers to the concentration of drug required to 50% of Jurkat T cells. Selectivity was calculated by dividing the B cell EC50 data by the that for the T cells. All measurements were conducted as described previously (see, e.g., T. Francis, et al., Bioorg. Med. Chem. Lett. 2006 16, 2423-2427; herein incorporated by reference in its entirety).

Example 3

This example demonstrates that 1,4-benzodiazepine-2,5-dione compounds of the present invention do not inhibit ATP synthesis. The following four compounds were exposed to cells, and ATP synthesis measured:

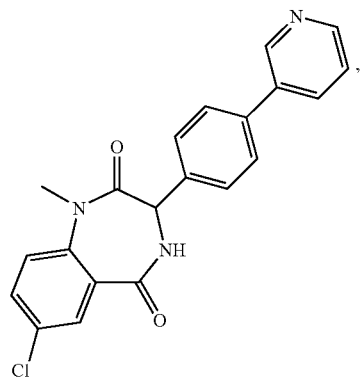

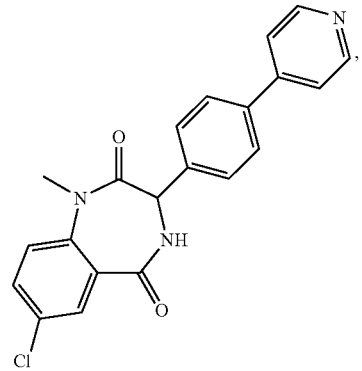

Figure 6:
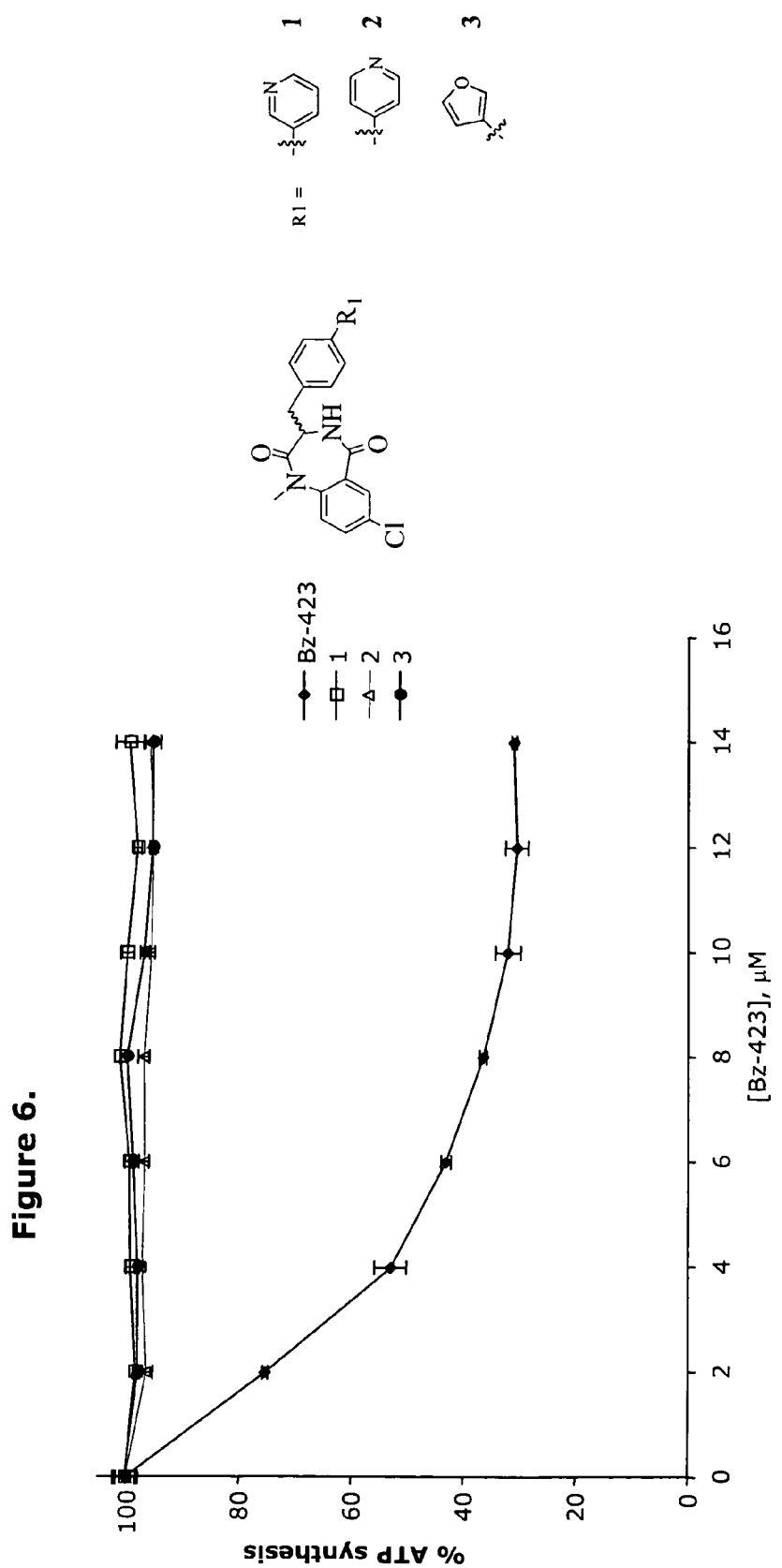
FIG. 6 shows cellular ATP synthesis in the presence of the compounds of the present invention.

51
-continued
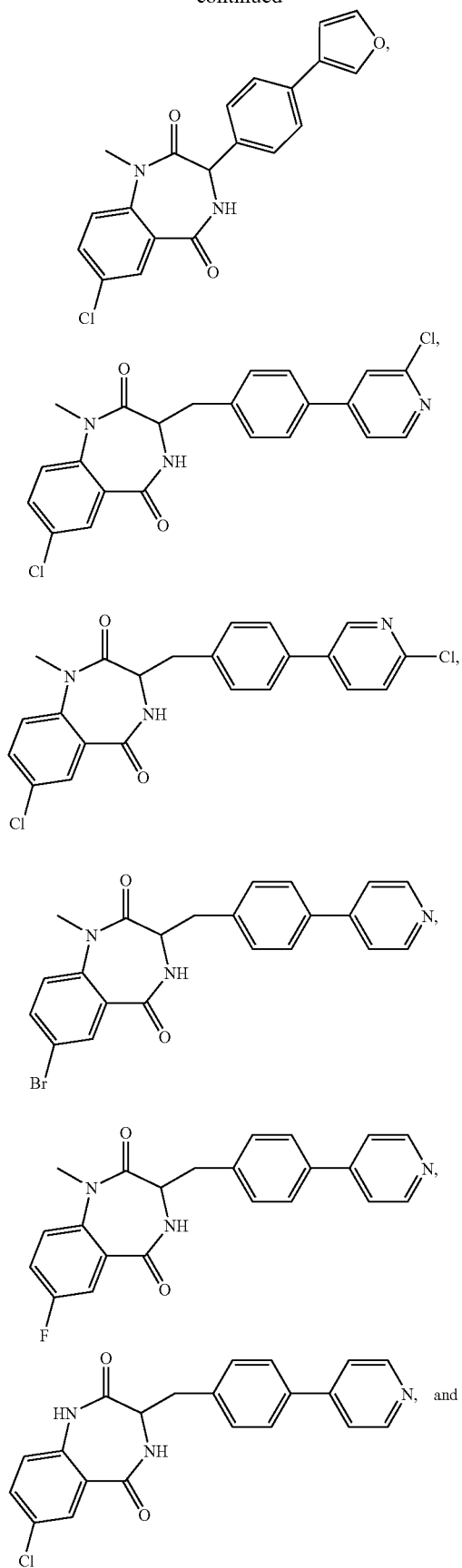
52
-continued
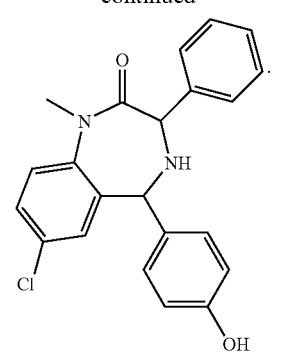
As shown in FIG. 6, the following compounds
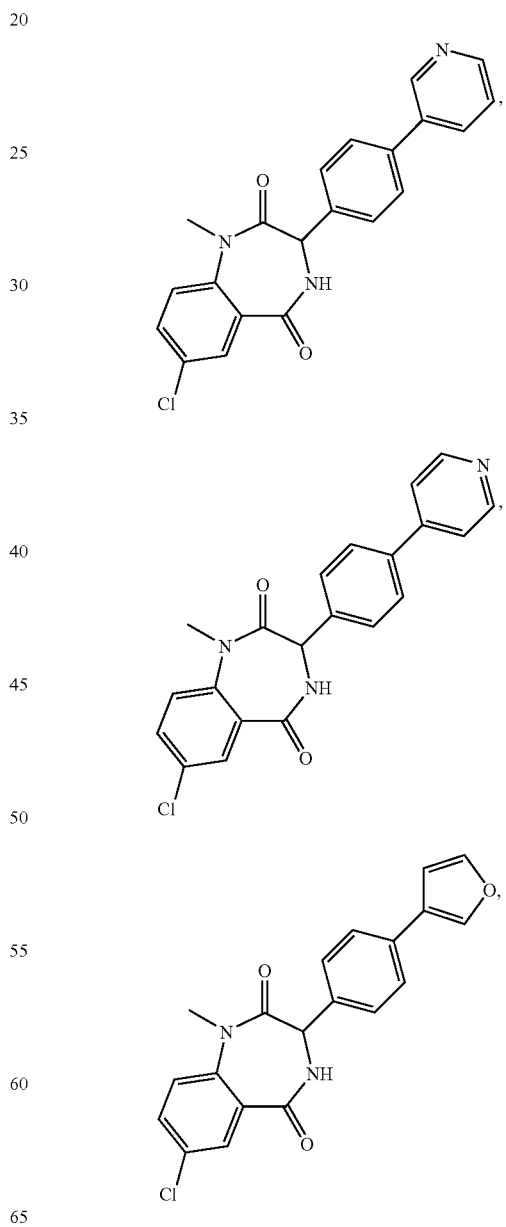
failed to inhibit ATP synthesis, while

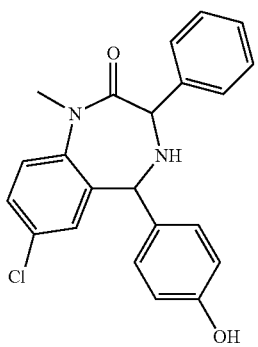

did inhibit ATP synthesis.

All publications and patents mentioned in the above specification are herein incorporated by reference. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A compound represented by the following formula:

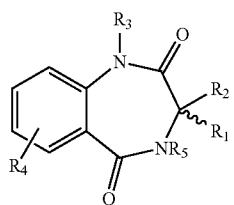

including R and S enantiomeric forms, racemic mixtures, and pharmaceutically acceptable salts thereof, wherein:

$R_1$ is

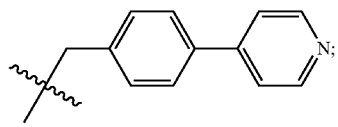

$R_2$ and $R_5$ are hydrogen;
$R_3$ is hydrogen or alkyl; and
$R_4$ is halogen.

2. The compound of claim 1, wherein said compound is selected from the group consisting of:

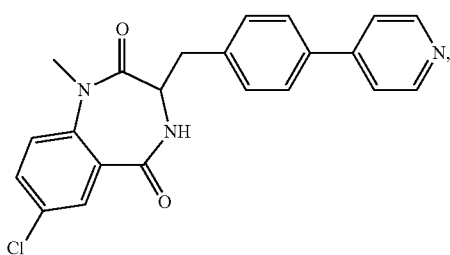

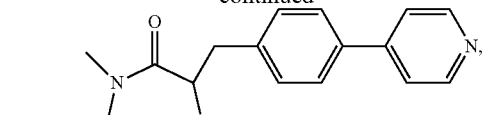

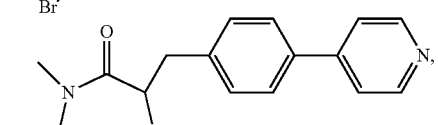

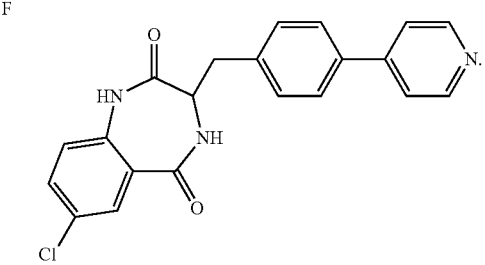

3. The compound of claim 1, wherein said compound is represented by:

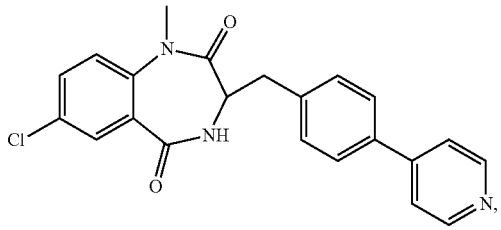

or a pharmaceutically acceptable salt thereof.

4. The compound of claim 1, wherein said compound is represented by:

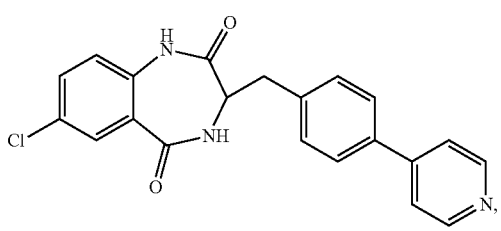

or a pharmaceutically acceptable salt thereof.

5. A pharmaceutical composition comprising a compound of claim 1 and a pharmaceutically acceptable carrier.

6. A method of treating a disorder selected from the group consisting of graft-versus-host disease, rheumatoid arthritis, Sjogren's syndrome, myasthenia gravis, asthma, psoriasis, cancer, systemic lupus erythematosus, multiple sclerosis, celiac sprue, idiopathic thrombocytopenia purpura, scleroderma, Crohn's Disease, inflammatory bowel disease, and ulcerative colitis, comprising administering an effective amount of a compound of claim 1 to a patient in need thereof to treat said disorder.

7. The method of claim 6, wherein the disorder is graft-versus-host disease or psoriasis.

8. The method of claim 6, wherein the disorder is rheumatoid arthritis.

9. The method of claim 6, wherein the disorder is Crohn's Disease, inflammatory bowel disease, or ulcerative colitis.

10. The method of claim 6, wherein the disorder is cancer.

11. The method of claim 6, wherein said compound is represented by:

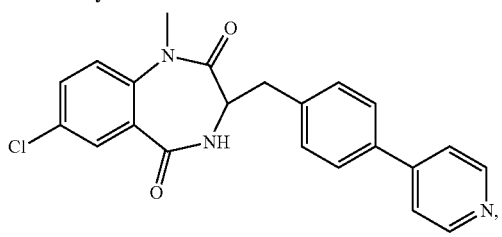

or a pharmaceutically acceptable salt thereof.

12. The method of claim 7, wherein said compound is represented by:

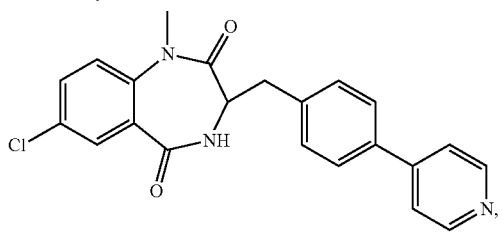

or a pharmaceutically acceptable salt thereof.

13. The method of claim 8, wherein said compound is represented by:

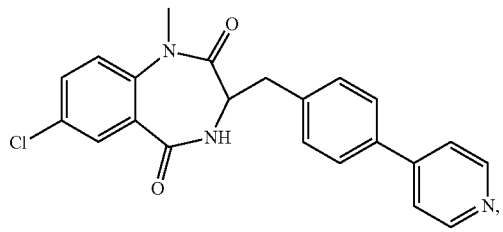

or a pharmaceutically acceptable salt thereof.

14. The method of claim 9, wherein said compound is represented by:

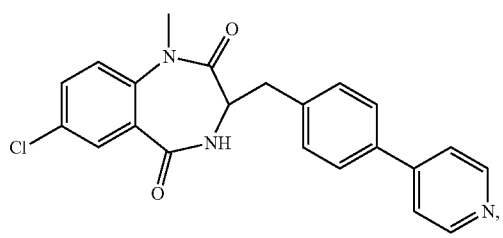

or a pharmaceutically acceptable salt thereof.

* * * * *